(12) United States Patent
Gotanda et al.

(10) Patent No.: US 10,349,903 B2
(45) Date of Patent: Jul. 16, 2019

(54) X-RAY COMPUTED TOMOGRAPHY APPARATUS

(71) Applicant: Toshiba Medical Systems Corporation, Otawara-shi (JP)

(72) Inventors: Katsumi Gotanda, Nasushiobara (JP); Kenji Tomomura, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 325 days.

(21) Appl. No.: 15/263,605

(22) Filed: Sep. 13, 2016

(65) Prior Publication Data

US 2017/0105696 A1  Apr. 20, 2017

(30) Foreign Application Priority Data

Oct. 20, 2015  (JP) .................................. 2015-206211
Sep. 1, 2016  (JP) .................................. 2016-171106

(51) Int. Cl.
*A61B 6/00* (2006.01)
*A61B 6/03* (2006.01)

(52) U.S. Cl.
CPC .............. *A61B 6/032* (2013.01); *A61B 6/461* (2013.01); *A61B 6/488* (2013.01); *A61B 6/5205* (2013.01); *A61B 6/4488* (2013.01)

(58) Field of Classification Search
CPC ....... A61B 6/032; A61B 6/037; A61B 6/4071; A61B 6/5235; A61B 6/027; A61B 6/035; A61B 6/12; A61B 6/4233; A61B 6/464; A61B 6/467; A61B 6/469; A61B 6/548; A61B 6/488; A61B 5/0073; A61B 5/0091; A61B 5/0095; A61B 5/0456; A61B 5/708; A61B 6/03; A61B 6/04; A61B 6/06; A61B 6/4028; A61B 6/4488; A61B 6/4007;

(Continued)

(56) References Cited

U.S. PATENT DOCUMENTS 6,102,567 A * 8/2000 Cabral ................. A61B 6/4233
378/146
7,003,070 B1 * 2/2006 Chen ....................... A61B 6/00
378/17

(Continued)

FOREIGN PATENT DOCUMENTS

JP  8-266650  10/1996
JP  10-277023  10/1998
JP  4-12055  1/2014

*Primary Examiner* — Irakli Kiknadze
(74) *Attorney, Agent, or Firm* — Oblon, McClelland, Maier & Neustadt, L.L.P.

(57) ABSTRACT

According to one embodiment, an X-ray CT apparatus includes a gantry, storage circuitry and control circuitry. The gantry including an X-ray tube is relatively movable on a floor surface of an examination room. The storage circuitry store information of a first boundary indicating an outer edge of a FOV inside the opening portion and information of a second boundary located between the first boundary and an inner surface of the opening portion to prevent interference between an object and the gantry. The control circuitry control the X-ray tube to stop emitting X-rays based on a relative positional relationship between a scan target area of the object and the first boundary or control the gantry to stop moving based on a relative positional relationship between a non-scan target area of the object and the second boundary.

9 Claims, 14 Drawing Sheets

(58) Field of Classification Search
CPC ....... A61B 6/507; A61B 6/583; A61B 6/0457; A61B 6/4014; A61B 6/4291; A61B 2503/40; A61B 6/025; A61B 6/541; A61B 6/4021; A61B 6/4447; A61B 6/504; A61B 6/461; A61B 6/5205; A61B 2090/037; A61B 5/4064; A61B 5/4076; A61B 5/417; A61B 5/4547; A61B 5/702; A61B 6/4035; A61B 6/405; A61B 6/4085; A61B 6/4241; A61B 6/4258; A61B 6/4429; A61B 6/4441; A61B 6/482; G01T 1/1615; G01T 1/1642
USPC ............... 378/4, 9, 10, 193–198, 8, 19, 98.8
See application file for complete search history.

(56) References Cited

U.S. PATENT DOCUMENTS

| | | | |
|---|---|---|---|
| 9,693,746 B2* | 7/2017 | Ancar | A61B 6/08 |
| 9,795,344 B2* | 10/2017 | Cho | A61B 6/405 |
| 2005/0053186 A1* | 3/2005 | Sukovic | A61B 6/032 378/4 |
| 2013/0064344 A1* | 3/2013 | Carol | A61B 6/032 378/10 |
| 2016/0183909 A1* | 6/2016 | Mehendale | A61B 6/08 378/205 |

* cited by examiner

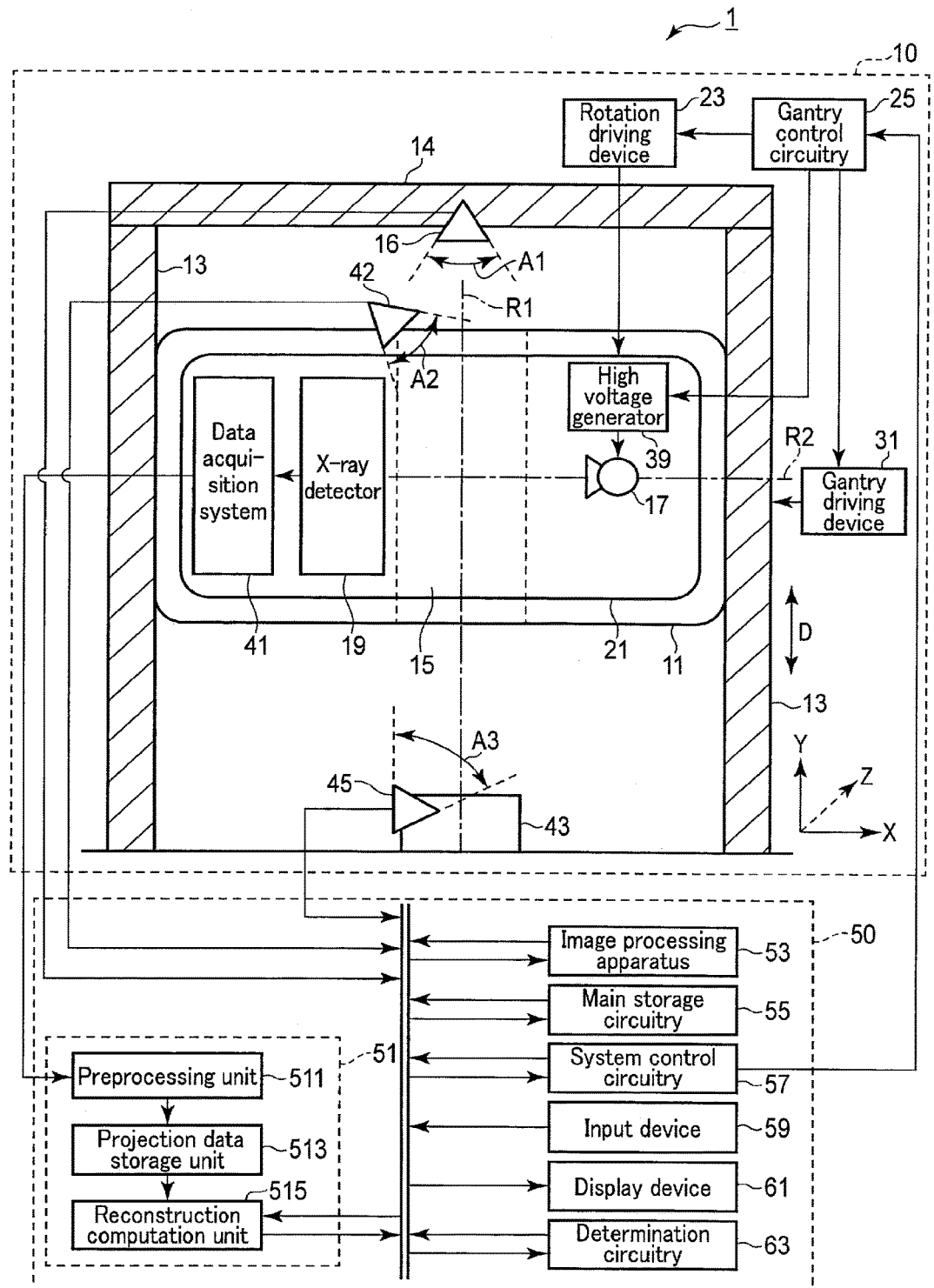
F I G. 1

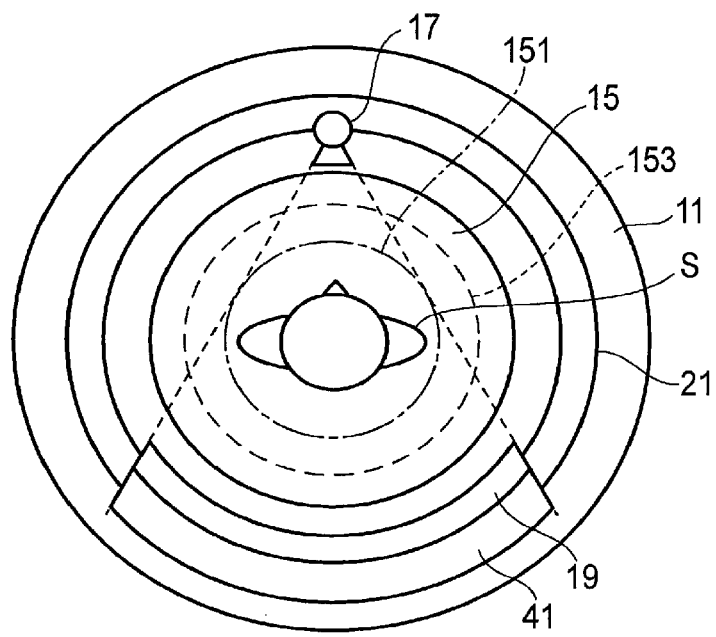
F I G. 2
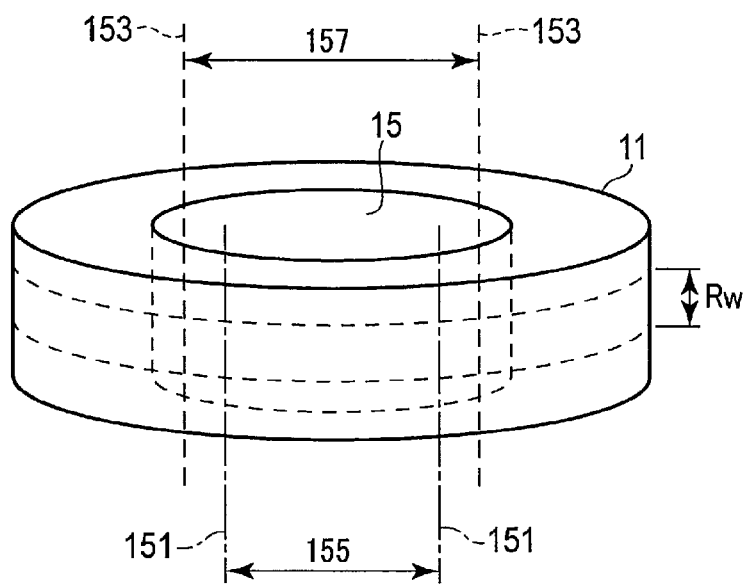
F I G. 3

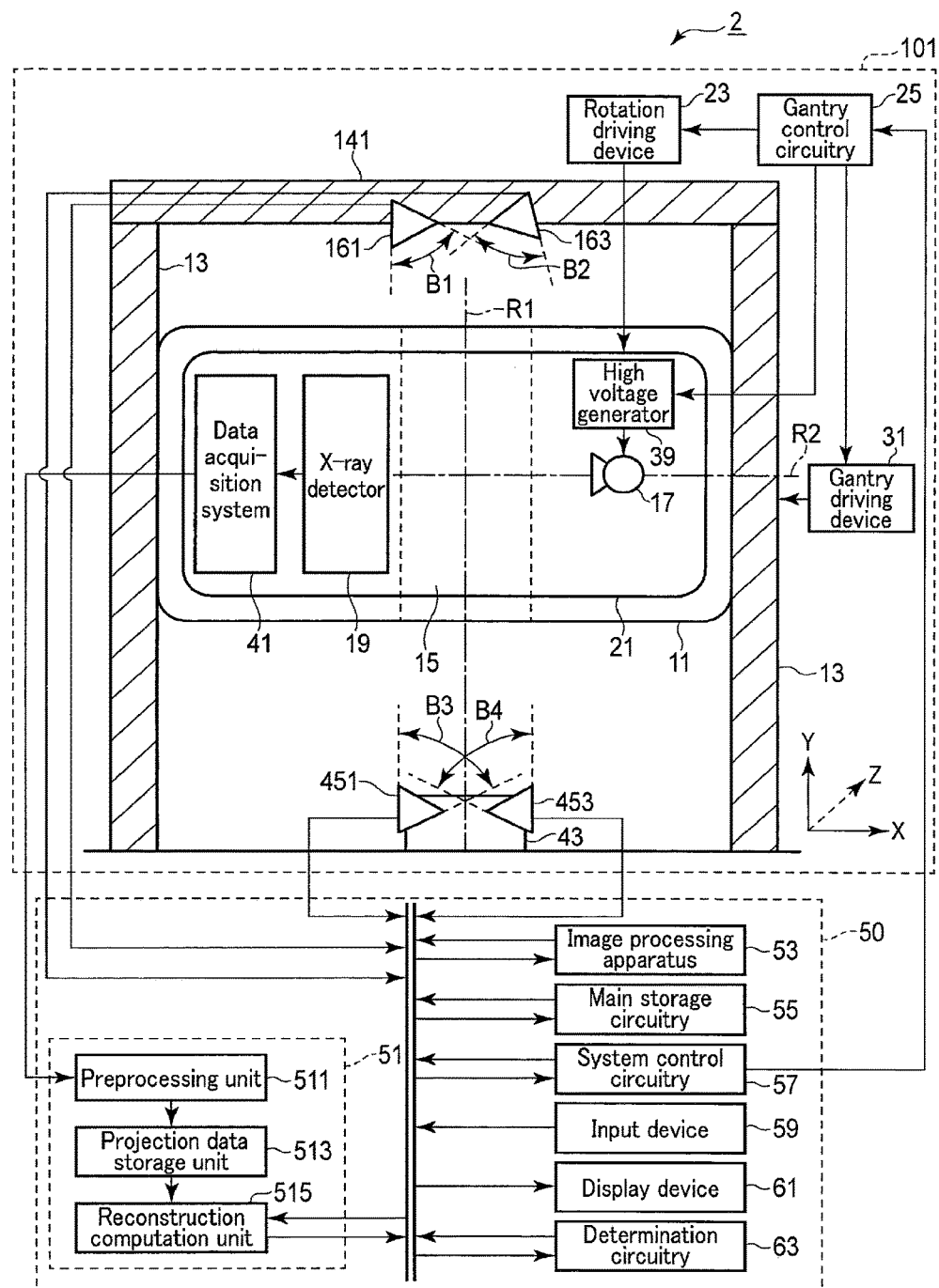
F I G. 7

X-RAY COMPUTED TOMOGRAPHY APPARATUS

CROSS-REFERENCE TO RELATED APPLICATIONS

This application is based upon and claims the benefit of priority from the prior Japanese Patent Applications No. 2015-206211, filed Oct. 20, 2015, and No. 2016-171106, filed Sep. 1, 2016, the entire contents of all of which are incorporated herein by reference.

FIELD

Embodiments described herein relate generally to an X-ray computed tomography apparatus.

BACKGROUND

Conventionally, X-ray computed tomography is generally performed while a patient is lying on a bed in a prone position. On the other hand, demands have arisen for an X-ray computed tomography for an object in a standing position.

When executing such computed tomography, a conventionally used X-ray computed tomography (CT) apparatus is tilted through 90°. At this time, when an object falls outside an imaging range, the acquired image cannot be used for diagnosis, resulting in unnecessary exposure to radiation.

When the gantry body of an X-ray CT apparatus placed in a horizontal position is lowered from the ceiling side, in order to check in advance whether the gantry body interferes with an object, chair-like bed, or the like, prevention apparatus which applies downward an interference examination light beam having a circumferential irradiation range having a predetermined radius smaller than the radius of an examination hole (gantry opening) into which the object is inserted.

In this case, if the predetermined radius is set to be equal to that of the imaging range by using the interference prevention apparatus in order to prevent unnecessary exposure to radiation, even when a portion other than the imaging area falls outside the imaging range, it is necessary to take measures such as stopping an imaging operation. This leads to prolongation of the imaging time.

BRIEF DESCRIPTION OF THE DRAWING

FIG. 1 is a block diagram showing the arrangement of an X-ray computed tomography apparatus according to the first embodiment;

FIG. 2 is a view showing an example of a detection range set for an object by an upper object detector provided on a horizontal brace according to the first embodiment;

FIG. 3 is a perspective view showing a gantry body, a first boundary, and a second boundary according to the first embodiment;

FIG. 7 is a block diagram showing the arrangement of an X-ray computed tomography apparatus according to the second embodiment;

DETAILED DESCRIPTION

Figure 4:
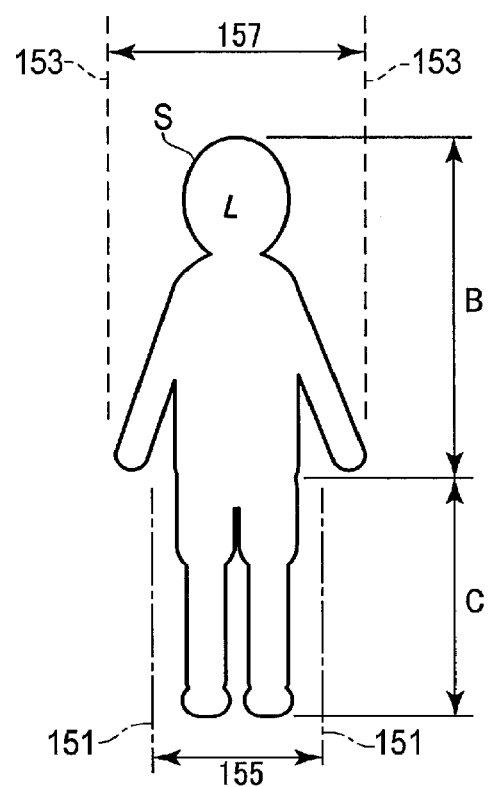
FIG. 4 is a view showing an example of a detection range set for an object by an opening object detector provided near the gantry body according to the first embodiment.

In general, according to one embodiment, an X-ray computed tomography apparatus includes a gantry, storage circuitry, and control circuitry. The gantry includes an X-ray tube and an X-ray detector on both sides of an opening portion. The gantry is relatively movable on a floor surface of an examination room to image an object with X-rays emitted from the X-ray tube. The storage circuitry stores information concerning a first boundary indicating an outer edge of a field of view inside the opening portion and stores information concerning a second boundary located between the first boundary and an inner surface of the opening portion to prevent interference between the object and the gantry. The control circuitry controls the X-ray tube so as to stop emitting X-rays based on a relative positional relationship between a scan target area of the object and the first boundary or controls the gantry so as to stop moving based on a relative positional relationship between a non-scan target area of the object and the second boundary.

(First Embodiment)

An X-ray computed tomography apparatus according to this embodiment will be described below with reference to the accompanying drawing.

FIG. 1 is a block diagram showing the arrangement of an X-ray computed tomography apparatus 1 according to this embodiment. As shown in FIG. 1, the X-ray computed tomography apparatus 1 according to the embodiment includes a gantry apparatus 10, a mounting base 43, and a console 50. For example, the gantry apparatus 10 and the mounting base 43 are installed in a CT examination room. In addition, the console 50 is installed in a control room adjacent to the CT examination room. The gantry apparatus 10 is communicatively connected to the console 50 wiredly or wirelessly. The gantry apparatus 10 is a scanning apparatus having an arrangement configured to perform X-ray computed tomography of an object in a standing or sitting position. The console 50 is a computer which controls the gantry apparatus 10.

The gantry apparatus 10 includes a gantry body 11 and columnar supports 13. In the following description, the vertical direction is defined as the Y direction. A direction horizontally perpendicular to a central axis R1 of an opening portion 15 and parallel to a horizontal axis R2 is defined as the X direction. A direction perpendicular to the Y and X directions is defined as the Z direction.

As shown in FIG. 1, the gantry body 11 is an almost cylindrical structure in which the opening portion 15 having an FOV (Field Of View) is formed. As shown in FIG. 1, the gantry body 11 accommodates an X-ray tube 17 and an X-ray detector 19 arranged to face each other through the opening portion 15. The gantry body 11 executes X-ray computed tomography of an object in a standing or sitting position. At this time, X-ray computed tomography may either be helical scanning or conventional scanning. X-ray computed tomography will be simply referred to as scanning hereinafter. The gantry body 11 can move relative to the floor surface of an examination room to image the object with X-rays emitted from the X-ray tube 17. The movement of the gantry body 11 will be described below. However, the mounting base 43 may be moved.

More specifically, the gantry body 11 further includes a main frame (not shown) formed from a metal such as aluminum and a rotating frame 21 supported by the main frame through a bearing and the like so as to be rotatable around a central axis R1. A portion of the main frame which is in contact with the rotating frame 21 is provided with an annular electrode (not shown). A conductive slider (not shown) is attached to the contact portion of the main frame so as to be in slidable contact with the annular electrode.

The rotating frame 21 is a metal frame formed from a metal such as aluminum and having an annular shape. For example, the X-ray tube 17 and the X-ray detector 19 are attached to the rotating frame 21. For example, the X-ray tube 17 and the X-ray detector 19 may be fitted in recess portions formed in the rotating frame 21 or may be fastened to it with fasteners such as screws.

The rotating frame 21 rotates at a constant angular velocity around the central axis R1 upon receiving a driving force from a rotation driving device 23. The rotation driving device 23 generates a driving force for rotating the rotating frame 21 under the control of gantry control circuitry 25. The rotation driving device 23 generates a driving force by being driven at a rotational speed corresponding to the duty ratio of a driving signal from the gantry control circuitry 25. The rotation driving device 23 is implemented by a motor such as a direct drive motor or servo motor. The rotation driving device 23 is accommodated in, for example, the gantry body 11.

As shown in FIG. 1, the columnar supports 13 are base members which support the gantry body 11 at a space from the floor surface. The columnar supports 13 are installed on the floor surface. The columnar supports 13 are structures which support the gantry body 11 so as to make it slidable in the longitudinal direction of the columnar supports 13. The columnar supports 13 each have a columnar shape such as a cylindrical shape or prismatic shape. The columnar supports 13 are formed from, for example, an arbitrary material such as a plastic or metal material. The columnar supports 13 are attached to side surface portions of the gantry body 11. The columnar supports 13 have a structure capable of supporting the gantry body 11 to make the central axis R1 of the opening portion 15 face in the vertical Y direction so as to scan an object in a standing or sitting position. The columnar supports 13 have a robust structure for supporting the gantry body 11.

Note that the columnar supports 13 are not limited to the above structure. For example, according to the above description, the columnar supports 13 each have a columnar shape. However, this embodiment is not limited to this. For example, the columnar supports 13 each may have any shape such as a U-shape as long as it can support at least one side portion of the gantry body. Note that the columnar supports 13 need not be fixed to the gantry body 11 so as to make the central axis R1 face in the vertical Y direction. That is, the columnar supports 13 may be configured to support the gantry body 11 so as to make it rotatable around a horizontal axis R2. More specifically, the columnar supports 13 and the gantry body 11 are connected through bearings and the like so as to make the gantry body 11 rotatable around the horizontal axis R2.

In addition, the columnar supports 13 may be configured to make the central axis R1 stationary at any angle with respect to the horizontal axis R2 as well as being able to support the gantry body 11 to make the central axis R1 have a posture remaining in the Y direction or Z direction.

As shown in FIG. 1, a gantry driving device 31 is connected to the columnar supports 13 to slide the gantry body 11 in the Y direction. The gantry driving device 31 generates a driving force for sliding the gantry body 11 in a longitudinal direction D under the control of the gantry control circuitry 25. More specifically, the gantry driving device 31 generates a driving force by being driven at a rotational speed corresponding to the duty ratio or the like of a driving signal from the gantry control circuitry 25.

Upon receiving a driving force from the gantry driving device 31, the columnar supports 13 slide/move the gantry body 11 along the longitudinal direction D. Upon receiving a driving force from the gantry driving device 31, the columnar supports 13 lower the gantry body 11 from the ceiling side of a CT examination room to the mounting base 43 before the start of scanning on an object. After the end of scanning on the object, the gantry driving device 31 causes the columnar supports 13 to raise the gantry body 11 from a scan position toward the ceiling of the CT examination room.

Note that a driving device for tiling the gantry body 11 (to be referred to as a tilt driving device hereinafter) may be connected to the columnar supports 13. The tilt driving device generates a driving force for rotating the gantry body 11 around the horizontal axis R2 in accordance with a driving signal from the gantry control circuitry 25. More specifically, the tilt driving device generates a driving force by being driven at a rotational speed corresponding to the duty or the like of a driving signal from the gantry control circuitry 25. The columnar supports 13 rotate the gantry body 11 around the horizontal axis R2 upon receiving a driving force from the tilt driving device. The gantry driving device 31 and the tilt driving device are implemented by, for example, motors such as serve motors.

As shown in FIG. 1, a horizontal brace (beam) 14 straddling on the two columnar supports 13, is provided on the upper ends of the two columnar supports 13 which support the gantry body 11 so as to make it slidable along the vertical Y direction. That is, the horizontal brace 14 straddles on the two columnar supports 13. An upper object detector 16 is mounted on the horizontal brace 14 at a position immediately above the opening portion 15.

The upper object detector 16 is preferably provided at a position on the central axis R1 on the horizontal brace 14. That is, the upper object detector 16 is provided above the opening portion 15. The upper object detector 16 is a device which can detect an object from immediately above the object along the vertical Y direction. The upper object detector 16 may detect end portions of the object (the vertex of the head, shoulders, the end portions of the extremities, elbows, and knees) or a contour of the overall object. The upper object detector 16 is, for example, a camera (a movie camera or video camera).

Note that the upper object detector 16 may have various types of distance sensors (optical (infrared and visible) sensors, a magnetic field (magnetic) sensor, an acoustic wave sensor, an ultrasonic sensor, and the like) for deciding the distance between itself and an object. Note that the upper object detector 16 may be formed from various types of circuitry and an optical system which are associated with motion capturing (motion sensor) to detect the position of an object.

The upper object detector 16 outputs information indicating whether an object is detected, the relative positional relationship between the opening portion 15 and the object, an upper image obtained by imaging the object, and the like to the console 50. At this time, the relative positional relationship between the position of the object and the gantry body 11 in the upper image is specified. Note that the upper object detector 16 may output information indicating whether an object is detected, a relative positional relationship, an upper image, and the like to the gantry control circuitry 25.

As shown in FIG. 1, the upper object detector 16 has a detection range Al capable of detecting the position of an object. Note that the upper object detector 16 may have the detection range Al capable of imaging a reference position or reference scale as a reference for the distance between itself and an object. The reference position or reference scale is, for example, an object which is stationary at the time of movement of the gantry body 11, and is provided on, for example, the mounting base 43. The upper object detector 16 may measure the distance to an object by detecting the reference scale.

In addition, when the horizontal brace 14 is not provided on the gantry apparatus 10, the upper object detector 16 may be provided on the ceiling of the CT examination room at a position immediately above the opening portion 15. At this time, the upper object detector 16 is preferably provided on the ceiling of the CT examination room at a position on the central axis R1. Note that a plurality of upper object detectors 16 may be provided on the horizontal brace 14 or the ceiling of the CT examination room.

FIG. 2 is a view showing an example of the detection range of an object S detected by the upper object detector 16. Referring to FIG. 2, a one-dot dashed line 151 indicates the boundary (to be referred to as the first boundary hereinafter) between the imaging range of the object S and a non-imaging range in the area (opening area) of the opening portion 15 of the gantry body 11. The inside of the one-dot dashed line 151 corresponds to an FOV (first area). That is, the inside of the one-dot dashed line 151 corresponds to the range in which an image can be reconstructed by an image reconstruction apparatus 51 (to be described later).

Referring to FIG. 2, a broken line 153 indicates the boundary (the second boundary to be referred to as an interference line hereinafter) between the first boundary 151 and the outer edge of the opening portion 15, which prevents interference between the object S and the gantry body 11. The outside of the interference line 153 indicates an area which can interfere with the gantry body 11. The inside of the interference line 153 indicates an area (to be referred to as a non-interference area (second area) hereinafter) which does not interfere with the gantry body 11.

The area between the first boundary 151 and the second boundary 153 corresponds to an area in which projection data necessary to reconstruct volume data may not be prepared by scanning (CT scanning) on the object S or a non-reconstruction area. Note that volume data corresponding to the area between the first boundary 151 and the second boundary 153 is called, for example, a mask area.

FIG. 3 is a perspective view showing the gantry body 11, the first boundary 151, and the second boundary 153. A range 155 in FIG. 3 indicates the diameter of the first boundary 151. The diameter 155 of the first boundary 151 is almost equal to the diameter of the FOV. A range 157 in FIG. 3 indicates the diameter of the second boundary 153. The diameter 157 of the second boundary 153 is smaller than that of the opening portion 15. A width Rw in FIG. 3 which is larger than the diameter 155 of the first boundary 151 corresponds to the width of an X-ray detector 19, i.e., the number of columns.

As shown in FIG. 1, the X-ray tube 17 generates X-rays upon receiving a high voltage from a high voltage generator 39. The high voltage generator 39 is attached to, for example, the rotating frame 21. The high voltage generator 39 generates a high voltage to be applied to the X-ray tube 17 under the control of the gantry control circuitry 25 from power supplied from a power supply device (not shown) of the gantry body 11 via the annular electrode. The high voltage generator 39 and the X-ray tube 17 are connected to each other via a high-voltage cable. The high voltage generated by the high voltage generator 39 is applied to the X-ray tube 17 via the high-voltage cable.

The X-ray detector 19 detects X-rays generated from the X-ray tube 17 and transmitted through the object S. The X-ray detector 19 is equipped with a plurality of X-ray detection elements (not show) arranged on a two-dimensional curved surface. Each X-ray detection element detects X-rays from the X-ray tube 17. Each X-ray detection element converts the detected X-rays into an electrical signal having a peak value corresponding to the intensity of the X-rays. Each X-ray detection element includes, for example, a scintillator and a photoelectric converter. The scintillator generates fluorescence upon receiving X-rays. The photoelectric converter converts the generated fluorescence into a charge pulse. The charge pulse has a peak value corresponding to the intensity of the generated X-rays.

Specifically, as a photoelectric converter, a device which converts photons into an electrical signal, such as a photomultiplier or photodiode, is used. Note that the X-ray detector 19 according to this embodiment is not limited to an indirect detection type detector which converts X-rays into fluorescence first and then converts the fluorescence into an electrical signal, and may be a direct detection type detector which directly converts X-rays into an electrical signal.

A data acquisition system (DAS) 41 acquires digital data indicating the intensity of X-rays attenuated by the object S for each view. The data acquisition system 41 is implemented by a semiconductor integrated circuit on which integration circuitry and an A/D converter provided for each of the plurality of X-ray detection elements are mounted in parallel. The data acquisition system 41 is connected to the X-ray detector 19 in the gantry body 11.

Each integration circuitry generates an integral signal by integrating an electrical signal from a corresponding X-ray detection element over a predetermined view period. Each A/D converter A/D-converts a generated integral signal to generate digital data having a data value corresponding to the peak value of the integral signal. Digital data after conversion is called raw data. Raw data is a set of the channel number and column number of an X-ray detection element as a data generation source and the digital value of an X-ray intensity identified by a view number indicating a view in which the data has been acquired. The raw data is supplied to the console 50 via, for example, a noncontact data transmitter (not shown) accommodated in the gantry body 11.

Note that in addition to the X-ray tube 17, the X-ray detector 19, the rotating frame 21, the main frame, the power supply device, the high voltage generator 39, and the data acquisition system 41 described above, the gantry body 11 may further accommodate various types of other devices necessary for scanning. For example, a cooling device for cooling the X-ray tube may be attached to the rotating frame 21. In addition, a fan for air conditioning may be attached to the gantry body 11.

An opening object detector 42 is provided on the outer edge of the opening portion 15 on the exterior of the gantry body 11. The opening object detector 42 is a device which can detect part of the object S located in the opening portion 15. The opening object detector 42 may detect end portions of the object S (the vertex of the head, shoulders, the end portions of the extremities, elbows, and knees) or a contour of the overall object. The opening object detector 42 is, for example, a camera (a movie camera or video camera).

Note that the opening object detector 42 may have various types of distance sensors (optical (infrared and visible) sensors, a magnetic field sensor, an acoustic wave sensor, an ultrasonic sensor, and the like) for deciding the distance between itself and the object S. Note that the opening object detector 42 may be formed from various types of circuitry and an optical system which are associated with motion capturing to detect the position of the object S.

The opening object detector 42 outputs information indicating whether the object S is detected in the opening portion 15, the relative positional relationship between the opening portion 15 and the object S, an opening image obtained by imaging the object S, and the like to the console 50. At this time, the relative positional relationship between the position of the object S and the gantry body 11 in the opening image is specified. Note that the opening object detector 42 may output information indicating whether the object S is detected, a relative positional relationship, an opening image, and the like to the gantry control circuitry 25.

As shown in FIG. 1, the opening object detector 42 has a detection range A2 capable of detecting the position of the object S in the opening portion 15. Note that the opening object detector 42 may have the detection range A2 capable of imaging a reference position or reference scale as a reference for the distance between itself and the object S. The reference position or reference scale is, for example, an object which is stationary at the time of movement of the gantry body 11, and is provided on, for example, the mounting base 43. The opening object detector 42 may measure the distance to the object S by detecting the reference scale. Note that a plurality of opening object detectors 42 may be provided on the exterior of the gantry body 11 and on the outer edge of the opening portion 15.

FIG. 4 is a view showing an example of the detection range of the object S detected by the opening object detector 42. A range B in FIG. 4 indicates a range outside an imaging target (which cannot be detected by the opening object detector 42) (to be referred to as a non-scan target area hereinafter) when scanning the object S. When scanning the object S, the non-scan target area is required not to fall outside the interference line (second boundary) 153. A range C in FIG. 4 indicates an imaging target range (to be referred to as a scan target area hereinafter) when scanning the object S. The scan target area is required not to fall outside the area defined by the first boundary 151, that is, the FOV.

Figure 5:
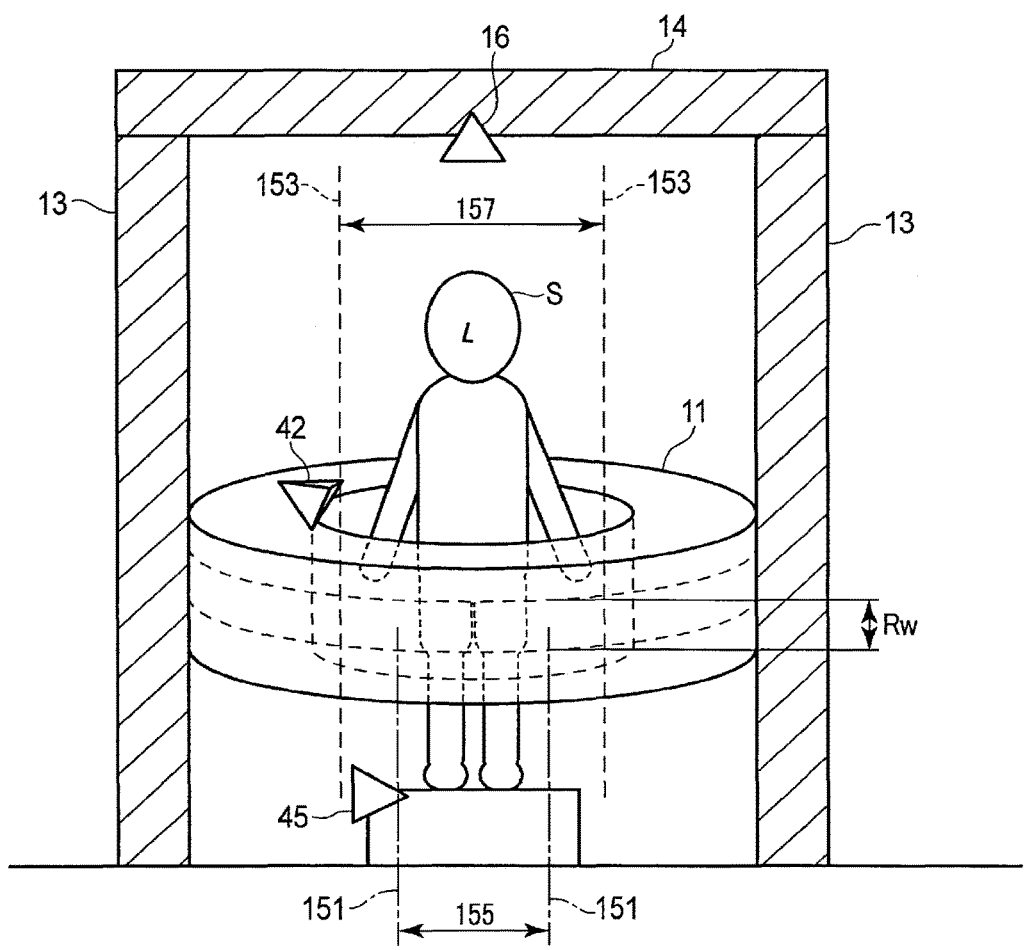
FIG. 5 is a detailed view for explaining FIG. 4 in more detail according to the first embodiment.

FIG. 5 is a detailed view for explaining FIG. 4 in more detail. As shown in FIG. 5, the non-scan target area is included in the non-interference area defined by the interference line 153. In addition, as shown in FIG. 5, the scan target area is included in the FOV (Field Of View). At this time, scanning is executed.

The gantry control circuitry 25 controls the high voltage generator 39, the rotation driving device 23, and the gantry driving device 31 under the control of system control circuitry 57 of the console 50. For example, the gantry control circuitry 25 controls the gantry body 11 and various types of devices mounted on the gantry apparatus 10 in accordance with determination results determined by determination circuitry 63 (to be described later). A specific control operation performed by the gantry control circuitry 25 with respect to the gantry apparatus 10 will be described in detail later.

The gantry control circuitry 25 includes, as hardware resources, various types of image processing apparatuses (processors) such as a CPU (Central Processing Unit) and an MPU (Micro Processing Unit) and various types of storage devices (memories and the like) such as a ROM (Read Only Memory) and a RAM (Random Access Memory).

In addition, the gantry control circuitry 25 may include an ASIC (Application Specific Integrated Circuit), an FPGA (Field Programmable Gate Array), a CPLD (Complex Programmable Logic Device, or SPLD (Simple Programmable Logic Device).

The processing apparatus implements the above functions by reading out and executing programs stored in the storage device. Note that programs may be directly embedded in the circuitry of the processing apparatus instead of being saved in the storage device. In this case, the processing apparatus implements the above functions by reading out and executing programs embedded in the circuitry.

Note that the gantry control circuitry 25 may be provided on the columnar support 13, the gantry body 11, or the console 50. Note that the gantry control circuitry 25 may control various types of circuitry and various types of units mounted on the gantry apparatus 10 in accordance with various types of instructions and information inputs which are input via an input device 59 provided on the exterior of the gantry body 11.

The mounting base 43 is provided on the floor surface of the CT examination room. The mounting base 43 is a structure which supports the object S in a standing or sitting position. That is, the object S is placed on the mounting base 43 in a standing or sitting position. The mounting base 43 has a robust structure for supporting the object S in a standing or sitting position. The mounting base 43 is formed from an arbitrary material such as a plastic or metal material.

Note that the upper end portion of the mounting base 43 may be formed from an artifact-free material, i.e., a material with a small X-ray attenuation coefficient. The mounting base 43 has a size corresponding to the diameter of the opening portion 15 immediately below the opening portion 15. This makes it possible to scan the object S placed on the mounting base 43 up to the lowermost end when the gantry body 11 moves downward to the lowermost end of the slidable movement range along the longitudinal direction D of the columnar support 13.

A lower object detector 45 is provided on the outer edge of the mounting base 43. That is, the lower object detector 45 is provided on the lower side of the opening portion 15. The lower object detector 45 is a device which can detect part of the object S placed in the opening portion 15. The lower object detector 45 is provided on the mounting base 43 so as to prevent the pinching of the object S as the gantry body 11 moves downward and to eliminate the blind spots of the detection range A1 of the upper object detector 16 and the detection range A2 of the opening object detector 42.

The lower object detector 45 may detect end portions of the object S (the vertex of the head, shoulders, the end portions of the extremities, elbows, and knees) or a contour of the overall object. The lower object detector 45 is, for example, a camera (a movie camera or video camera). Note that if the mounting base 43 is not installed, the lower object detector 45 is installed on the floor surface of the CT examination room at, for example, a position near the position immediately below the opening portion 15.

Note that the lower object detector 45 may have various types of distance sensors (optical (infrared and visible) sensors, a magnetic field sensor, an acoustic wave sensor, and an ultrasonic sensor) for deciding the distance between itself and the object S. In addition, the lower object detector 45 may be formed from various types of circuitry and an optical system which are associated with motion capturing to detect the position of the object S.

The lower object detector 45 outputs information indicating whether the object S is detected in the opening portion 15, the relative positional relationship between the opening portion 15 and the object S, a lower image obtained by imaging the object S, and the like to the console 50. At this time, the relative positional relationship between the position of the object S and the gantry body 11 in the lower image is specified. Note that the lower object detector 45 may output information indicating whether the object S is detected, a relative positional relationship, a lower image, and the like to the gantry control circuitry 25.

As shown in FIG. 1, the lower object detector 45 has a detection range A3 capable of detecting the position of the object S in the opening portion 15. Note that the lower object detector 45 may have the detection range A3 capable of imaging a reference position or reference scale as a reference for the distance between itself and the object S. The reference position or reference scale is, for example, an object which is stationary at the time of movement of the gantry body 11, and is provided on, for example, the ceiling of the CT examination room or the horizontal brace 14. The lower object detector 45 may measure the distance to the object S by detecting the reference scale. In addition, a plurality of lower object detectors 45 may be provided on the outer edge of the mounting base 43 or the like.

As shown in FIG. 1, the console 50 includes the image reconstruction apparatus 51, an image processing apparatus 53, main storage circuitry 55, the system control circuitry 57, the input device 59, a display device 61, and the determination circuitry 63 which are connected to each other via a bus. Data communication between the image reconstruction apparatus 51, the image processing apparatus 53, the main storage circuitry 55, the system control circuitry 57, the input device 59, the display device 61, and the determination circuitry 63 is performed via the bus.

The image reconstruction apparatus 51 reconstructs a CT image concerning the object S based on raw data from the console 50. More specifically, the image reconstruction apparatus 51 includes a preprocessing unit 511, a projection data storage unit 513, and a reconstruction computation unit 515. The image reconstruction apparatus 51 is controlled by, for example, the system control circuitry 57.

The preprocessing unit 511 preprocesses raw data from the console 50. Preprocessing includes various types of correction processing such as logarithmic conversion, X-ray intensity correction, and offset correction. Raw data after preprocessing is called projection data. The projection data storage unit 513 is a storage device such as an HDD, SSD, or integrated circuit storage device which stores projection data generated by the preprocessing unit 511.

The reconstruction computation unit 515 generates a CT image expressing the spatial distribution of CT values concerning the object S based on projection data. As an image reconstruction algorithm, there may be used an existing image reconstruction algorithm such as an analytical image reconstruction method such as an FBP (Filtered Back Projection) method or CBP (Convolution Back Projection) method or a statistical image reconstruction method such as an ML-EM (Maximum Likelihood Expectation Maximization) method or OS-EM (Ordered Subset Expectation Maximization) method.

The image reconstruction apparatus 51 includes a processing apparatus (processors) such as a CPU, an MPU, and a GPU (Graphics Processing Unit) and storage devices (memories) such as a ROM and a RAM as hardware resources. In addition, the image reconstruction apparatus 51 may be implemented by an ASIC, FPGA, CPLD, or SPLD. The processing apparatus implements the functions of the preprocessing unit 511 and the reconstruction computation unit 515 by reading out and executing programs saved in the storage device.

Note that programs may be directly embedded in the circuitry of the processing apparatus instead of being saved in the storage device. In this case, the processing apparatus implements the functions of the preprocessing unit 511 and the reconstruction computation unit 515 by reading out and executing programs embedded in the circuitry. Alternatively, dedicated hardware circuitry functioning as the preprocessing unit 511 and dedicated hardware circuitry functioning as the reconstruction computation unit 515 may be mounted in the image reconstruction apparatus.

The image processing apparatus 53 performs various types of image processing for a CT image reconstructed by the image reconstruction apparatus 51. For example, when the CT image is volume data, the image processing apparatus 53 performs three-dimensional image processing such as volume rendering, surface volume rendering, image value projection processing, MPR (Multi Planar Reconstruction), CPR (Curved MPR) processing, and MIP (Maximum Intensity Projection) for the CT image to generate a display image. The image processing apparatus 53 outputs the generated display image to the display device 61.

Note that the image processing apparatus 53 may generate a three-dimensional object image (coordinate data of the object) based on outputs from a plurality of object detectors (the upper object detector 16, the opening object detector 42, and the lower object detector 45). In addition, the image processing apparatus 53 may extract end portions of the object S or a contour of the overall object S by using outputs (images) from a plurality of object detectors.

The image processing apparatus 53 includes processing apparatuses (processors) such as a CPU, an MPU, and a GPU and storage devices (memories) such as a ROM and a RAM as hardware resources. In addition, the image processing apparatus 53 may be implemented by an ASIC, FPGA, CPLD, or SPLD. Note that the image processing apparatus 53 and the image reconstruction apparatus 51 may be integrated on a single substrate in the console 50.

The image reconstruction apparatus 51, the image processing apparatus 53, the system control circuitry 57, and the console 50 may be integrated on a single substrate or distributed and mounted on a plurality of substrates.

The main storage circuitry 55 is a storage device such as an HDD, SSD, or integrated circuit storage device which stores various types of information. In addition, the main storage circuitry 55 may be a driving device which reads and writes various types of information from and in portable storage media such as a CD-ROM drive, DVD drive, and flash memory. The main storage circuitry 55 stores reconstructed images (volume data) reconstructed by the image reconstruction apparatus 51 and medical images processed by the image processing apparatus 53.

The main storage circuitry 55 also stores an upper image generated by the upper object detector 16, an opening image generated by the opening object detector 42, and a lower image generated by the lower object detector 45. The main storage circuitry 55 stores a scan plan transmitted from an RIS (Radiology Information System) via an interface and a network (neither of which is shown).

The main storage circuitry 55 stores programs concerning scanning according to this embodiment, gantry control programs for controlling the gantry apparatus 10 based on outputs from a plurality of object detectors and the first boundary 151 and the second boundary (interference line) 153 set in advance, and the like. The main storage circuitry 55 stores programs and determination conditions concerning a plurality of types of determination executed by the determination circuitry 63.

The main storage circuitry 55 stores a coordinate system concerning the gantry apparatus 10 (to be referred to as a gantry coordinate system hereinafter). The main storage circuitry 55 stores coordinate data concerning the first boundary 151 (to be referred to as the first boundary data hereinafter) and coordinate data concerning the second boundary (interference line) 153 (to be referred to as the second boundary data hereinafter) in the gantry coordinate system. The main storage circuitry 55 may store a coordinate specifying program for specifying (extracting) coordinate data concerning part of the object S (to be referred to as object coordinate data hereinafter) in each of an upper image, an opening image, and a lower image. In this case, part of the object S is a region, of a contour of the object S, which can be end portions, such as the vertex of the head, shoulders, the end portions of the extremities, elbows, and knees.

The main storage circuitry 55 stores the positional relationship between the first boundary 151, the second boundary 153, and the gantry apparatus 10. For example, the main storage circuitry 55 stores information concerning the first boundary indicating the outer edge of a field of view inside the opening portion 15 and information concerning the second boundary which is located between the first boundary and the inner surface of the opening portion 15 and prevents interference between the object S and the gantry body 11. Note that the first boundary 151 and the second boundary (interference line) 153 can be changed as needed via the input device 59. The main storage circuitry 55 stores a scanography position and an imaging range along the vertical Y direction which are input in accordance with instructions issued by the operator via the input device 59. The main storage circuitry 55 also stores predetermined warnings corresponding to determination results obtained by the determination circuitry 63. The predetermined warnings may be, for example, determination results themselves and take display forms which call attention from the operator.

The system control circuitry 57 includes processing apparatuses (processors) such as a CPU, an MPU, and a GPU and storage devices (memories) such as a ROM and a RAM as hardware resources. The system control circuitry 57 functions as the main unit of the X-ray computed tomography apparatus 1 according to this embodiment. More specifically, the system control circuitry 57 reads out various types of programs stored in the main storage circuitry 55, loads them in the memory, and controls each unit and each circuitry of the X-ray computed tomography apparatus 1 in accordance with the loaded control programs.

The system control circuitry 57 also controls various types of devices and various types of circuitry in accordance with various types of instructions and information inputs which are input via the input device 59. The system control circuitry 57 may execute a function concerning the determination circuitry 63. The system control circuitry 57 reads out a warning corresponding to a determination result from the main storage circuitry 55. The system control circuitry 57 outputs the readout warning to the display device 61.

The input device 59 includes input interface circuitry which receives various types of instructions, information inputs, and the like from the operator. As the input device 59, a keyboard, a mouse, various types of switches, and the like can be used. The input device 59 outputs various types of instructions and information inputs which are input by the operator to the system control circuitry 57. Note that the input device 59 may be provided on the console 50 or the gantry apparatus 10. The input device provided on the gantry apparatus 10 outputs various types of instructions, information inputs, and the like input by the operator to the gantry control circuitry 25. For example, the input device 59 inputs a change, resetting, and the like concerning the first boundary 151 and the second boundary (interference line) 153. The input device 59 also inputs an instruction to start scanning, an instruction to resume the scanning, and the like. Note that the input device 59 may input a setting or change concerning a specified portion of the object S in each of an upper image, an opening image, and a lower image.

The display device 61 includes display circuitry which displays various types of information such as a two-dimensional CT image and a display image. As the display device 61, it is possible to use, for example, a CRT display, liquid crystal display, organic EL display, LED display, plasma display, or another arbitrary display known in this technical field. The display device 61 displays a predetermined warning corresponding to a determination result. In addition, if the non-scan target area exceeds the interference line at the time of scanning, the display device 61 may display information indicating that there is a problem in terms of the accuracy of scanning.

Before the movement (downward) of the gantry body 11 to a scanography position, the determination circuitry 63 determines, by using an upper image and a lower image, whether the object S is placed on the mounting base 43. While the object S is placed on the mounting base 43 and the gantry body 11 is moved (downward) to the scanography position, the determination circuitry 63 determines, based on the positional relationship between each of the upper and lower images, the position of the object S, and the second boundary (interference line) 153, whether the object S is located in the second area, i.e., in the non-interference area. Note that an opening image may further be used for the above determination.

More specifically, the determination circuitry 63 extracts (specifies) object coordinate data in each of the upper image, the opening image, and the lower image. At this time, the extracted object coordinate data is associated with the area of the object S (a scan target area and a non-scan target area). More specifically, the scan target area corresponds to object coordinate data included in the imaging range (to be referred to as scan target coordinate data hereinafter) in the opening image when the gantry body 11 reaches the scanography position.

In addition, the non-scan target area corresponds to object coordinate data which is not included in the imaging range (to be referred to non-scan coordinate data hereinafter) in the upper and lower images when the gantry body 11 reaches the scanography position. This executes separation between the scan target area and the non-scan target area in the object S. Note that the extracted object coordinate data is data indicating coordinates corresponding to the gantry coordinate system.

The determination circuitry 63 compares the scan target coordinate data with the first boundary data to determine whether the scan target area is located in the first area (FOV). The determination circuitry 63 also compares the non-scan coordinate data concerning each of the upper and lower images with the second boundary data to determine whether the non-scan target area is located in the second area (non-interference area). That is, the determination circuitry 63 executes the above determination by using the coordinates (boundary position information) of the first boundary 151 and the second boundary 153 in the gantry coordinate system and the object coordinate data (object coordinate information). Determination performed by the determination circuitry 63 will be described in more detail below.

In response to the arrival of the gantry body 11 at the scanography position, the determination circuitry 63 determines, based on the positional relationship between the position of the object S and the first boundary 151 in an opening image, whether the scan target area is located in the first area (FOV). That is, the determination circuitry 63 determines, based on the scan target coordinate data and the first boundary data, whether the scan target coordinate data is located in the FOV.

During scanning on the scan target area of the object S by the gantry body 11, the determination circuitry 63 determines, based on the positional relationship (coordinate relationship) between the position of the scan target area and the first boundary 151 in the opening image, whether the scan target area is located in the FOV. That is, at the arrival of the gantry body 11 at the scanography position and during scanning on the scan target area, the determination circuitry 63 determines, based on the positional relationship (coordinate relationship) between the scan target coordinate data and the first boundary data, whether the scan target area is located in the FOV.

During scanning on the scan target area, the determination circuitry 63 determines, based on the positional relationship between the position of the non-scan target area and the second boundary (interference line) 153 in each of the upper and lower images, whether the non-scan target area is located in the non-interference area. That is, during scanning on the scan target area, the determination circuitry 63 determines, based on the relative positional relationship (coordinate relationship) between the non-scan coordinate data and the second boundary data, whether the non-scan target area is located in the non-interference area.

The determination circuitry 63 outputs the determination result to the gantry control circuitry 25. Note that the determination circuitry 63 may output the determination result to the system control circuitry 57. The determination circuitry 63 includes processing apparatuses (processors) such as a CPU and an MPU and storage devices (memories) such as a ROM and a RAM as hardware resources. In addition, the determination circuitry 63 may be implemented by an ASIC, FPGA, CPLD, or SPLD. Note that the determination circuitry 63 may be incorporated in the system control circuitry 57, the gantry control circuitry 25, or the like.

(Gantry Control Function)

The gantry control function is a function of controlling the gantry apparatus 10 to control the movement of the gantry body 11 concerning scanning and the scanning based on a determination result output from the determination circuitry 63. Processing concerning the gantry control function will be called gantry control processing. The function of the gantry control circuitry 25 concerning gantry control processing will be described in detail.

The gantry control circuitry 25 controls the gantry apparatus 10 based on a determination result obtained by the determination circuitry 63. The gantry control circuitry 25 controls the gantry apparatus 10 to perform scanning and move and stop the gantry body 11 based on the positional relationship between the position of the object S and the first boundary 151 during scanning on the object S by the gantry body 11. That is, the gantry control circuitry 25 controls the gantry apparatus 10 to perform scanning and move and stop the gantry body 11 based on the result of determination on the comparison between scan target coordinate data and the first boundary data during scanning on the scan target area.

In other words, the gantry control circuitry 25 controls the X-ray tube 17 to stop emitting X-rays based on the relative positional relationship between the scan target area of the object S and the first boundary. In addition, the gantry control circuitry 25 controls the gantry body 11 to stop moving based on the relative positional relationship between the non-scan target area of the object S and the second boundary. For example, when part of the scan target area exceeds the first boundary, the gantry control circuitry 25 controls the X-ray tube 17 to stop emitting X-rays. In addition, when part of the non-scan target area exceeds the second boundary, the gantry control circuitry 25 controls the gantry body 11 to stop moving.

More specifically, upon determining that the object S placed on the mounting base 43 is located in the non-interference area before the downward movement of the gantry body 11 to the scanography position, the gantry control circuitry 25 controls the gantry driving device 31 to move the gantry body 11 downward to the scanography position in response to the input of an instruction to move the gantry body 11 to the scanography position. The gantry body 11 starts to move downward to the scanography position under the control of the gantry control circuitry 25 with respect to the gantry driving device 31.

During movement (downward) of the gantry body 11 to the scanography position, upon determining that the non-scan target area is located in the non-interference area, i.e., the non-scan coordinate data is located in the non-interference area defined by the second boundary data, the gantry control circuitry 25 controls the gantry driving device 31 and the like to continue the downward movement of the gantry body 11. The gantry control circuitry 25 controls the gantry driving device 31 to continue the downward movement of the gantry body 11 toward the scanography position.

During the movement (downward) of the gantry body 11 to the scanography position, upon determining that part of the object S is located outside the non-interference area, i.e., the non-scan coordinate data is located outside the non-interference area defined by the second boundary data, the gantry control circuitry 25 controls the gantry driving device 31 to stop moving the gantry body 11. The gantry control circuitry 25 controls the gantry driving device 31 to stop the downward movement of the gantry body 11.

Upon determining that the non-scan target area is located in the non-interference area, i.e., the non-scan coordinate data is located in the non-interference area defined by the second boundary data, after the stoppage of the downward movement of the gantry body 11, the gantry control circuitry 25 controls the gantry driving device 31 to move the gantry body 11 to the scanography position again in response to an instruction to resume the movement via the input device 59. The gantry control circuitry 25 controls the gantry driving device 31 to resume the downward movement of the gantry body 11 toward the scanography position.

After the gantry body 11 has arrived at the scanography position, upon determining that the scan target area is located in the FOV, i.e., the scan target coordinate data is located in the FOV defined by the first boundary data, the gantry control circuitry 25 controls the gantry apparatus 10 to start to scan the scan target area in response to a scan start instruction issued by the operator via the input device 59.

More specifically, the gantry control circuitry 25 controls the high voltage generator 39, the rotation driving device 23, and the like to start scanning. When scanning to be started is conventional scanning, the gantry body 11 does not move. When scanning to be started is helical scanning, the gantry control circuitry 25 further controls the gantry driving device 31 to move (or reciprocate) the gantry body 11 into a preset imaging range.

During scanning on the scan target area, upon determining that the scan target area is located in the FOV, the gantry control circuitry 25 controls the gantry apparatus 10 to continue scanning. During the scanning, the non-scan target area is located outside the detection range of the opening object detector 42 and hence may be located at any position. That is, since the non-scan target area need not be located in the FOV during scanning, the scanning continues regardless of the position of the non-scan target area.

During scanning on a scan target area, upon determining that part of the scan target area is located outside the FOV, i.e., the scan target coordinate data is located outside the FOV defined by the first boundary data, the gantry control circuitry 25 controls the gantry apparatus 10 to stop scanning. More specifically, the gantry control circuitry 25 controls the high voltage generator 39 to stop irradiating the scan target area of the object S with X-rays. The gantry control circuitry 25 controls the high voltage generator 39 to stop scanning. At this time, the gantry control circuitry 25 controls the rotation driving device 23 to stop the rotation of the rotating frame 21.

Note that when executed scanning is helical scanning, the gantry control circuitry 25 controls the gantry driving device 31 to stop the movement of the gantry body 11. The gantry driving device 31 stops the movement of the gantry body 11 during scanning under the control of the gantry control circuitry 25 with respect to the gantry driving device 31.

Upon determining that the scan target area is located in the FOV after the stoppage of scanning, the gantry control circuitry 25 controls the high voltage generator 39, the rotation driving device 23, and the like in response to an instruction to resume the scanning via the input device 59. The gantry control circuitry 25 controls the high voltage generator 39, the rotation driving device 23, and the like to resume the scanning on the scan target area.

Figure 6A:
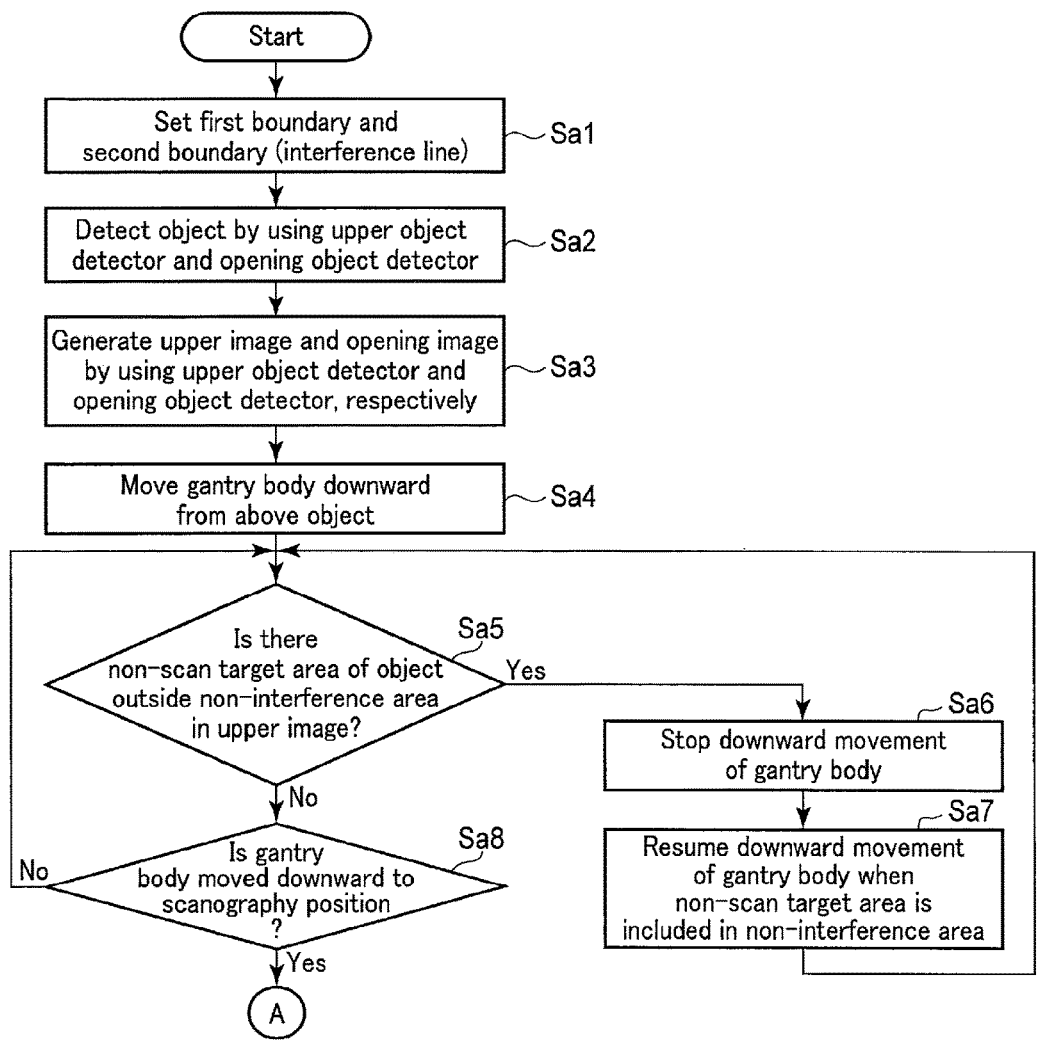
FIG. 6A is a flowchart showing a processing procedure for gantry control processing according to the first embodiment.
Figure 6B:
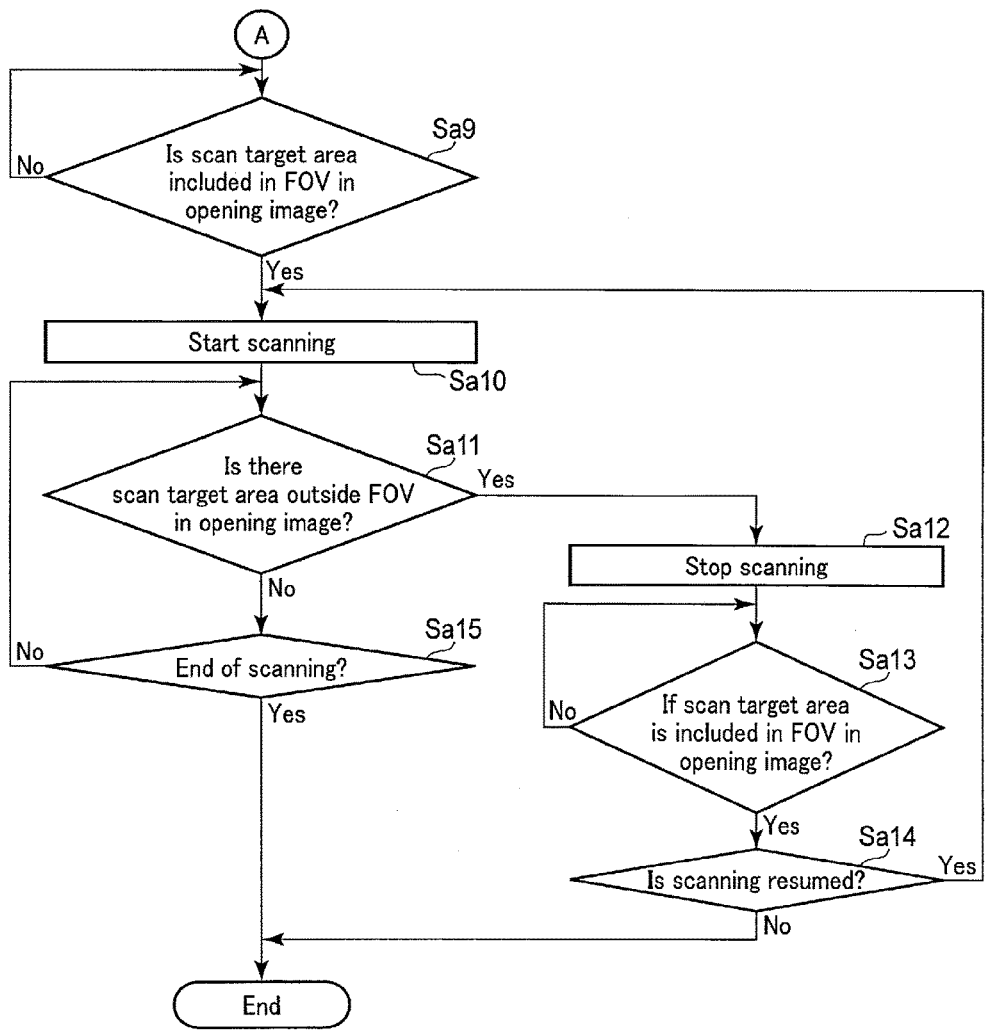
FIG. 6B is a flowchart showing a processing procedure for gantry control processing according to the first embodiment.

FIGS. 6A and 6B are flowcharts showing an example of a processing procedure for gantry control processing.

The first boundary 151 and the second boundary 153 are set (step Sa1). At this time, the main storage circuitry 55 outputs first boundary data and second boundary data to the determination circuitry 63. The upper object detector 16, the opening object detector 42, and the lower object detector 45 detect the object S (step Sa2). Note that if these object detectors do not detect the object S, the subsequent processing is not executed. After the processing step Sa2, the upper object detector 16 generates an upper image. In addition, the opening object detector 42 generates an opening image (step Sa3). The lower object detector 45 generates a lower image.

At this time, non-scan coordinate data is extracted from the upper and lower images. The extracted non-scan coordinate data are associated with the non-scan target area of the object S. This specifies a non-scan target area. In addition, scan target coordinate data is extracted from the opening image. The extracted scan target coordinate data is associated with the target area in the scan target area of the object S. This specifies the scan target area.

The non-scan coordinate data concerning the upper and lower images is compared with the second boundary data. If it is determined by this comparison that the object S is included in the non-interference area, the gantry body 11 is moved downward toward to scanography position in response to an instruction to move the gantry downward which is issued by the operator via the input device 59 (step Sa4).

If the non-scan target area is located outside the non-interference area in the upper image (step Sa5), i.e., the non-scan coordinate data is located outside a closed curve defined by the boundary data of the second boundary 153, the downward movement of the gantry body 11 is stopped (step Sa6). At this time, a predetermined warning is displayed on the display device 61. The predetermined warning can be any notification as long as the operator can be notified that "the object has fallen outside the interference line". When the non-scan coordinate data is included in the inside of the closed curve defined by the boundary data of the second boundary 153 and the operator has input an instruction to resume the downward movement via the input device 59, the downward movement of the gantry body 11 is resumed (step Sa7).

If there is no non-scan target area outside the non-interference area in the upper image (step Sa5), the gantry body 11 is moved downward to the scanography position (step Sa8). If the scan target area is not included in the FOV in the opening image (step Sa9), i.e., the scan target coordinate data is included in the inside (FOV) of a closed curve defined by the boundary data of the first boundary 151, scanning is started in accordance with an instruction to start scanning issued by the operator via the input device 59 (step Sa10).

If there is a scan target area outside the FOV in the opening image (step Sa11), i.e., there is scan target coordinate data outside a closed curve defined by the boundary data of the first boundary 151, scanning (exposure) is stopped (step Sa12). At this time, when scanning is helical scanning, the movement of the gantry body 11 is also stopped. In addition, a predetermined warning is displayed on the display device 61. The predetermined warning may be any warning as long as the operator can be notified that "the scan target area has fallen outside the FOV".

If the scan target area is included in the FOV in the opening image (step Sa13), i.e., the scan target coordinate data is included in the inside (FOV) of a closed curve defined by the boundary data of the first boundary 151 and a scan resume instruction is input by the operator via the input device 59 (step Sa14), scanning is resumed. If the scanning is not resumed, the scanning is stopped.

If there is no scan target area outside the FOV in the opening image (step Sa11), i.e., the scan target coordinate data is included inside (FOV) of a closed curve defined by the boundary data of the first boundary 151, scanning is executed until the issuance of a scan end instruction (step Sa15).

According to the above arrangement, the following effects are obtained.

The X-ray computed tomography apparatus 1 according to this embodiment includes the sensor (object detector) which detects the object S, and determines, based on boundary position information and object position information associated with the gantry body 11 of the X-ray computed tomography apparatus 1, whether scan target coordinate data is included in the FOV. If the scan target area falls outside the FOV, the apparatus can stop scanning. If the scan target area returns into the FOV, the apparatus can resume the scanning. In addition, the apparatus can display a predetermined warning in accordance with the stoppage of the gantry body 11 and the stoppage of scanning.

In addition, the X-ray computed tomography apparatus 1 according to this embodiment determines whether the non-scan target area is outside the interference line to avoid interference with the gantry body 11. If the non-scan target area is outside the interference line, the apparatus can stop the vertical movement of the gantry body 11. If the non-scan target area returns into the interference line, the apparatus can resume the vertical movement of the gantry body 11.

That is, the X-ray computed tomography apparatus 1 according to this embodiment checks by itself at which height the gantry body 11 is located relative to the object S, and determines whether an area outside the FOV is a scan target area. This makes it possible to stop the scanning or display a predetermined warning. The X-ray computed tomography apparatus 1 according to the embodiment therefore can secure safety for the object S and allows observation of a scan target area while suppressing unnecessary exposure of the object S without requiring a long scan time.

As described above, this embodiment can provide the X-ray computed tomography apparatus 1 which prevents interference between the object S and the gantry body 11 and can reduce unnecessary exposure of the object S.

(Modification)

This modification is configured to execute the gantry control function upon selecting a control mode of controlling the movement of the gantry body 11 in accordance with a change in field of view.

The main storage circuitry 55 stores a program concerning the first control mode and a program concerning the second control mode. The first control mode is a control mode of controlling the X-ray tube 17 to stop emitting X-rays when part of a scan target area exceeds the first boundary and controlling the gantry body 11 to stop moving when a non-scan target area exceeds the second boundary. The second control mode is a control mode of controlling the gantry body 11 to stop moving when a contour of the object S exceeds the second boundary. The main storage circuitry 55 may store a correspondence table of the sizes of fields of view with respect to tilt angles.

The input device 59 inputs an instruction to change the size of the field of view. The size of the field of view is changed by, for example, a predetermined operation with respect to a scan range corresponding to a scanogram in a screen for scan planning which is displayed on the display device 61. The input device 59 inputs an instruction to decide a changed field of view. The input device 59 outputs the decided size of the field of view to the determination circuitry 63.

The input device 59 inputs an instruction to tilt the gantry body 11 relative to the floor surface of the examination room. A tilt instruction may be input by pressing a switch provided on the exterior of the gantry body 11 or performing the operation of setting the tilt of a scan range relative to a scanogram on the screen for scan planning which is displayed on the display device 61. The input device 59 outputs the size of the field of view corresponding to the tilt angle based on the tilt instruction to the determination circuitry 63. Note that the system control circuitry 57 may decide the size of the field of view in accordance with a tilt angle by using the correspondence table stored in the main storage circuitry 55. If, for example, the field of view on a plane parallel to the rotation axis of the rotating frame 21 and the vertical direction is a rectangle, the shape (size) of the field of view based on the tilt of the gantry body 11 is a parallelogram obtained by cutting this rectangle rotated in accordance with the tilt angle with a straight line which passes through two vertices, of the four vertices of the rotated rectangle, which are nearest to the rotation axis, and is parallel to the rotation axis.

The determination circuitry 63 compares the contour of the object S with the size of the field of view in the upper image and the opening image. With this comparison, the determination circuitry 63 determines whether the contour of the object S is included in the field of view. That is, the determination circuitry 63 executes this determination by using the position information of the first boundary 151 and the object position information concerning a change in field of view after the change. The determination circuitry 63 outputs the determination result to the gantry control circuitry 25. Note that the determination circuitry 63 may output the determination result to the system control circuitry 57.

Figure 11:
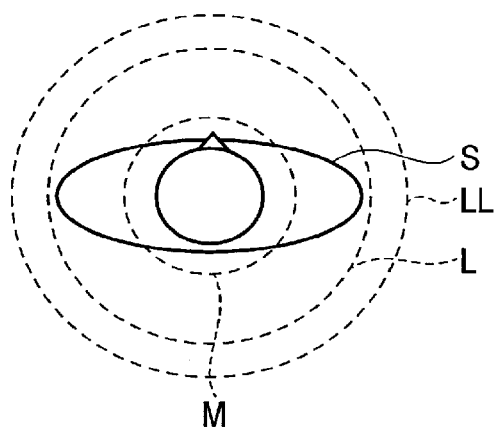
FIG. 11 is a view for explaining a control mode concerning the movement of the gantry body according to a modification of the first embodiment.

FIG. 11 is a view showing the positional relationship between the field of view and the contour of the object S when viewed from the Y direction. FIG. 11 shows a maximum field of view LL. The maximum field of view LL encloses the contour of the object S. A field of view L shown in FIG. 11 is narrower than the maximum field of view LL. Like the maximum field of view LL, the field of view L encloses the contour of the object S. In the maximum field of view LL and the field of view L, the determination circuitry 63 determines that the contour of the object S is included the field of view. A field of view M shown in FIG. 11 is narrower than the field of view L. The field of view M does not enclose the contour of the object S. In the field of view M, the determination circuitry 63 determines that the contour of the object S is not included in the field of view.

If the decided field of view, i.e., the field of view changed in accordance with a setting made by the operator, is narrower than the contour of the object S, the gantry control circuitry 25 reads out the second control mode from the main storage circuitry 55. The gantry control circuitry 25 then executes the movement of the gantry body 11 in the second control mode. In addition, if the decided field of view, i.e., the field of view changed in accordance with a setting made by the operator, is wider than the contour of the object S, the gantry control circuitry 25 reads out the first control mode from the main storage circuitry 55. The gantry control circuitry 25 then executes the movement of the gantry body 11 in the first control mode. Note that the system control circuitry 57 may control the movement of the gantry body 11 in the first control mode or the second control mode.

(Gantry Control Function)

Figure 12:
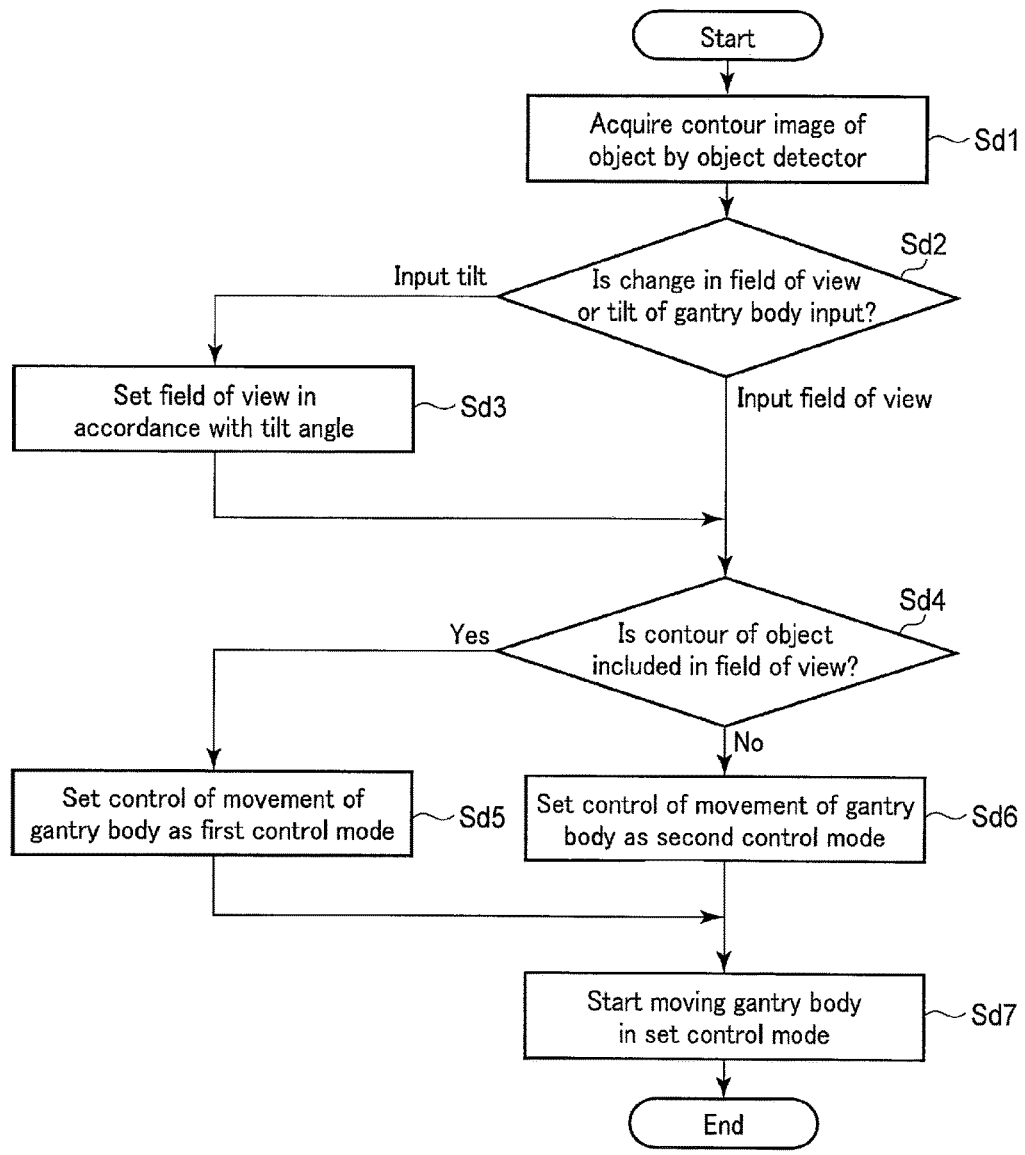
FIG. 12 is a flowchart showing a setting procedure for a control mode concerning the movement of the gantry body according to a modification of the first embodiment.

The gantry control function according to this modification is a function of controlling the gantry apparatus 10 to control the movement and scanning of the gantry body 11 based on a determination result corresponding to a change in field of view. FIG. 12 is a flowchart showing an example of a procedure for setting a control mode concerning the movement of the gantry body 11 according to this modification.

The object detector acquires a contour image (an upper image, an opening image, or the like) of the object S in advance (step Sd1). The information of the contour of the object S is output to the determination circuitry 63. An input to change the field of view or the tilt of the gantry body 11 is input via the input device 59 (step Sd2). When the tilt of the gantry body 11 is input, a field of view is set in accordance with the tilt angle (step Sd3). After a field of view corresponding to the tilt angle is set or a field of view is input, it is determined by using the contour image whether the contour of the object S is included in the field of view (step Sd4).

If the contour of the object S is included in the field of view (YES in step Sd4), the system control circuitry 57 reads out a program concerning the first control mode from the main storage circuitry 55 in response to an input indicating determination of inclusion from the determination circuitry 63. With this operation, a control mode for the movement of the gantry body 11 is set to the first control mode (step Sd5). If the contour of the object S is not included in the field of view (NO in step Sd4), the system control circuitry 57 reads out a program concerning the second control mode from the main storage circuitry 55 in response to an input indicating determination of inclusion from the determination circuitry 63. With this operation, a control mode for the movement of the gantry body 11 is set to the second control mode (step Sd6). The movement of the gantry body 11 is started in the set control mode (step Sd7).

According to the above arrangement, the following effects are obtained.

The X-ray computed tomography apparatus 1 according to this embodiment can select and set a control mode concerning control of the movement of the gantry body 11 in accordance with a change in field of view. That is, in accordance with a change in field of view based on an instruction from the operator or a change in field of view accompanying the tilt of the gantry body 11, the X-ray computed tomography apparatus 1 compares the size of the changed field of view with the contour of the object S to determine whether the contour of the object S is included in the field of view, thereby deciding (switching) a control mode concerning the movement of the gantry body 11. With this operation, the X-ray computed tomography apparatus 1 can control the movement of the gantry body 11 in accordance with the relationship of inclusion between the size of the field of view and the contour of the object S while reducing unnecessary exposure of the object S without any interference between the object S and the gantry.

(Second Embodiment)

The second embodiment differs from the first embodiment in that it is not equipped with the opening object detector 42, and executes the determination in the first embodiment by specifying a non-scan target area and a scan target area based on an imaging area set in a scanogram.

FIG. 7 is a block diagram showing the arrangement of an X-ray computed tomography apparatus 2 according to this embodiment. In the following description, the same reference numerals denote constituent elements having almost the same functions and arrangements, and a repetitive description will be made only when required.

A first upper object detector 161 and a second upper object detector 163 are mounted on a horizontal brace 141. More specifically, the first upper object detector 161 and the second upper object detector 163 are installed on the horizontal brace 141 at symmetrical positions (line-symmetrical positions) on both the sides of a central axis R1. Note that when the horizontal brace 141 is not provided on a gantry apparatus 101, the first upper object detector 161 and the second upper object detector 163 may be provided on the ceiling of the CT examination room at line-symmetrical positions on both the sides of the central axis R1. The number of object detectors provided on the horizontal brace 141 is not limited to two.

The first upper object detector 161 outputs information indicating whether an object is detected, the relative positional relationship between an opening portion 15 and the object, a first upper image obtained by imaging the object, and the like to a console 50. At this time, the relative positional relationship between the position of an object (non-scan coordinate data) in the first upper image and the gantry body 11 (gantry coordinate system) is specified. Note that the first upper object detector 161 outputs information indicating whether an object is detected, a relative positional relationship, the first upper image, and the like to a gantry control circuitry 25.

The second upper object detector 163 outputs information indicating whether an object is detected, the relative positional relationship between the opening portion 15 and the object, the second upper image obtained by imaging the object, and the like to the console 50. At this time, the relative positional relationship between the position of the object (the non-scan coordinate data) in the second upper image and a gantry body 11 (gantry coordinate system) is specified. Note that the second upper object detector 163 may output information indicating whether the object is detected, a relative positional relationship, the second upper image, and the like to the gantry control circuitry 25 and the like.

As shown in FIG. 7, the first upper object detector 161 has a detection range B1 capable of detecting the position of the object. Note that the first upper object detector 161 may have the detection range B1 capable of imaging a reference position or reference scale as a reference for the distance between itself and the object.

As shown in FIG. 7, the second upper object detector 163 has a detection range B2 capable of detecting the position of an object. Note that the second upper object detector 163 may have the detection range B2 capable of detecting a reference position or reference scale as a reference for the distance between itself and the object. The detection range B1 and the detection range B2 are defined by, for example, almost the same angle.

A first lower object detector 451 and a second lower object detector 453 are provided on the outer edge of a mounting base 43 at symmetrical positions (line-symmetrical positions) on both the sides of the central axis R1. Note that if the mounting base 43 is not provided on the gantry apparatus 101, the first lower object detector 451 and the second lower object detector 453 may be provided on the floor surface of the CT examination room at symmetrical positions on both the sides of the central axis R1. Note that the number of object detectors provided on the mounting base 43 is not limited to two.

The first lower object detector 451 outputs information indicating whether an object is detected, the relative positional relationship between the opening portion 15 and the object, the first lower image obtained by imaging the object, and the like to the console 50. At this time, the relative positional relationship between the position of an object S (non-scan coordinate data) in the first lower image and the gantry body 11 is specified. Note that the first lower object detector 451 may output information indicating whether an object is detected, a relative positional relationship, the first lower image, and the like to the gantry control circuitry 25.

The second upper object detector 163 outputs information indicating whether the object is detected, the relative positional relationship between the opening portion 15 and the object, the second lower image obtained by imaging the object, and the like to the console 50. At this time, the relative positional relationship between the position of the object (non-scan coordinate data) and the gantry body 11 in the second lower image is specified. Note that the second lower object detector 453 may output information indicating whether the object is detected, a relative positional relationship, the second lower image, and the like to the gantry control circuitry 25.

As shown in FIG. 7, the first lower object detector 451 has a detection range B3 capable of detecting the position of the object. Note that the first lower object detector 451 may have the detection range B3 capable of imaging a reference position or reference scale as a reference for the distance between itself and the object.

As shown in FIG. 7, the second lower object detector 453 has a detection range B4 capable of detecting the position of the object. Note that the second lower object detector 453 may have the detection range B4 capable of a reference position or reference scale as a reference for the distance between itself and the object. The detection range B3 and the detection range B4 are defined by an almost equal angle.

The image processing apparatus 53 generates a scanogram based on data output from the data acquisition system 41 when performing scanography. The generated scanogram is output to a display device 61.

The display device 61 displays the scanogram. At this time, the display device 61 superimposes and displays, on the scanogram, two boundary lines for setting the boundary of a scan range in the scanogram.

Figure 8:
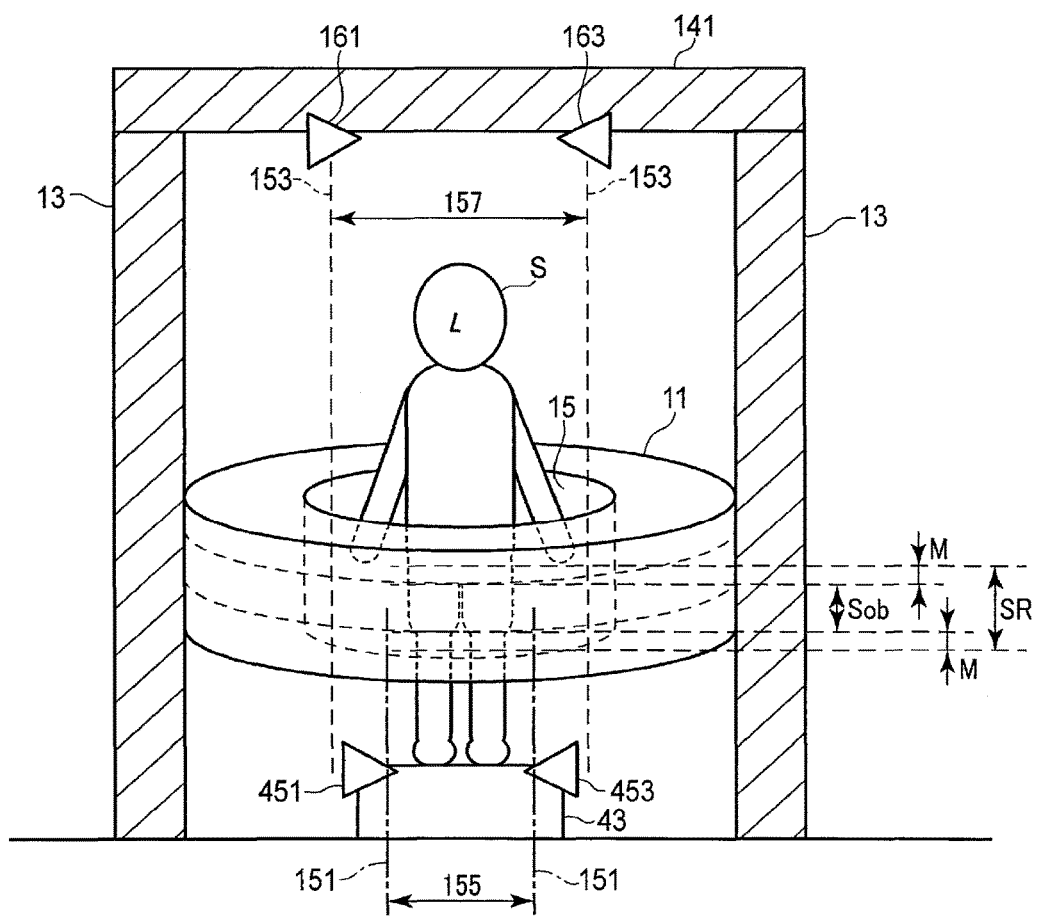
FIG. 8 is a perspective view showing a scan range according to the second embodiment.

The input device 59 inputs an instruction to perform scanography of the object. An input device 59 inputs a scan range with respect to the displayed scanogram in accordance with an instruction from the operator. For example, the input device 59 decides a scan range by moving the two boundary lines in accordance with an instruction from the operator. Note that a scan range may be decided with predetermined margins being provided for a scan target area. FIG. 8 is a perspective view showing an example of a scan range. As shown in FIG. 8, a scan range SR has margins M with respect to a width Sob of the scan target area. The margins M correspond to the difference between the scan arrange SR and the width Sob of the scan target area.

A system control circuitry 57 controls each unit, each circuitry, each device, and the like concerning the X-ray computed tomography apparatus 2 to execute scanography in response to an input of a scanography instruction. The system control circuitry 57 controls each unit, each circuitry, each device, and the like concerning the X-ray computed tomography apparatus 2 to execute scanning on a scan range set in a scanogram.

The system control circuitry 57 associates the set scan range with the gantry coordinate system by aligning them with each other. With this operation, the system control circuitry 57 can grasp the relative position between the object S and the gantry body 11 at the time of scanning. The system control circuitry 57 specifies a scan target area (scan target coordinate data) based on the scan range, and the first upper image, the second upper image, the first lower image, and the second lower image acquired at the time of scanography. The system control circuitry 57 outputs information concerning the specified scan target area (scan target coordinate data) to the determination circuitry 63.

The system control circuitry 57 decides, as non-scan coordinate data (non-scan target area), object coordinate data whose position information of the scan range set by using a scanogram does not match (mismatch, inconsistency) position information (object coordinate data) of the object S obtained by the object detectors (first upper object detector 161, the second upper object detector 163, the first lower object detector 451, and the second lower object detector 453). The system control circuitry 57 outputs information (scan target coordinate data) concerning the specified scan target area to the determination circuitry 63. Note that the determination circuitry 63 or the gantry control circuitry 25 may determine (specify) the above scan target area and the non-scan target area.

The determination circuitry 63 determines, by using the first upper image, the second upper image, the first lower image, and the second lower image, whether the object S is placed on the mounting base 43, before the movement (downward) of the gantry body 11 to the scanography position. While the object S is placed on the mounting base 43 and the gantry body 11 is moved (downward) to the scanography position, the determination circuitry 63 determines whether the object S is located in the second area (non-interference area), based on the positional relationship between a second boundary (interference line) 153 and the position of the object S in each of the first upper image, the second upper image, the first lower image, and the second lower image.

More specifically, the determination circuitry 63 extracts (specifies) object coordinate data from each of the first upper image, the second upper image, the first lower image, and the second lower image. The determination circuitry 63 compares the object coordinate data with the second boundary data to determine whether there is non-scan coordinate data outside the second area (non-interference area). That is, the determination circuitry 63 executes this determination by using the coordinates (boundary position information) of the second boundary 153 in the gantry coordinate system and the object coordinate data (object position information).

When the gantry body 11 reaches the scanography position during scanography, the determination circuitry 63 compares the object coordinate data with the second boundary data to determine whether there is object coordinate data outside the second area (non-interference area).

When the gantry body 11 reaches the scanography position during scanning on the scan target area, the determination circuitry 63 determines, based on the positional relationship between the position of the scan target area specified by a scanogram and the first boundary 151, whether the scan target area is located inside the first area (FOV).

When the gantry body 11 has reached the scanography position during scanning on the scan target area, if the position information (object coordinate data) of the object S acquired by the object detector does not match the position information of the scan range set by using a scanogram, i.e., the gantry body 11 has not reached the scan range, the determination circuitry 63 determines whether the non-scan coordinate data is located inside the second boundary (non-interface area).

If the determination circuitry 63 determines that the object S placed on the mounting base 43 is located inside the non-interference area before the downward movement of the gantry body 11 to the scanography position, the gantry control circuitry 25 controls a gantry driving device 31 to move the gantry body 11 downward to the scanography position in response to an input of an instruction to move the gantry body 11 to the scanography position. The gantry body 11 starts to move downward to the scanography position under the control of the gantry control circuitry 25 with respect to the gantry driving device 31.

During movement (downward) of the gantry body 11 to the scanography position, if it is determined that the non-scan target area is located inside the non-interference area, i.e., the non-scan coordinate data is located inside the non-interference area defined by the second boundary data, the gantry control circuitry 25 controls the gantry driving device 31 and the like to continue the downward movement of the gantry body 11. The gantry control circuitry 25 controls the gantry driving device 31 to continue the downward movement of the gantry body 11 to the scanography position.

During the movement (downward) of the gantry body 11 to the scanography position, if it is determined that part of the object S is located outside the non-interference area, i.e., the non-scan coordinate data is located outside the non-interference area defined by the second boundary data, the gantry control circuitry 25 controls the gantry driving device 31 to stop the movement of the gantry body 11. The gantry control circuitry 25 controls the gantry driving device 31 to stop the downward movement of the gantry body 11.

After the downward movement of the gantry body 11 is stopped, if it is determined that the non-scan target area is located inside the non-interface area, i.e., the non-scan coordinate data is located inside the non-interference area defined by the second boundary data, the gantry control circuitry 25 controls the gantry driving device 31 to move the gantry body 11 to the scanography position again in response to an input of an instruction to resume the movement issued via the input device 59. The gantry control circuitry 25 controls the gantry driving device 31 to resume the downward movement of the gantry body 11 toward the scanography position.

After the gantry body 11 reaches the scanography position, if it is determined that the object S is located in the FOV, i.e., the object coordinate data is located in the FOV defined by the first boundary data, the gantry control circuitry 25 controls the gantry apparatus 101 to start scanography in response to an instruction to start scanography issued by the operator via the input device 59. More specifically, the gantry control circuitry 25 controls the high voltage generator 39 and the rotation driving device 23 to start scanography.

During the movement of the gantry body 11 to the scanography position after scanography, if it is determined that the non-scan target area is located inside the non-interference area, i.e., the non-scan coordinate data is located inside the non-interference area defined by the second boundary data, the gantry control circuitry 25 controls the gantry driving device 31 and the like to continue the movement of the gantry body 11. The gantry control circuitry 25 controls the gantry driving device 31 to continue the downward movement of the gantry body 11 to the scanography position.

During the movement of the gantry body 11 to the scanography position, if it is determined that part of the object S is located outside the non-interference area, i.e., the non-scan coordinate data is located outside the non-interference area defined by the second boundary data, the gantry control circuitry 25 controls the gantry driving device 31 to stop the movement of the gantry body 11. The gantry control circuitry 25 controls the gantry driving device 31 to stop the movement of the gantry body 11.

After the stoppage of the movement of the gantry body 11 to the scanography position, if it determined that the non-scan target area is located inside the non-interference area, i.e., the non-scan coordinate data is located inside the non-interference area defined by the second boundary data, the gantry control circuitry 25 controls the gantry driving device 31 to resume the movement of the gantry body 11 to the scanography position in response to an instruction to resume the movement issued via the input device 59. The gantry control circuitry 25 controls the gantry driving device 31 to resume the movement of the gantry body 11 toward the scanography position.

(Gantry Control Function)

Figure 9A:
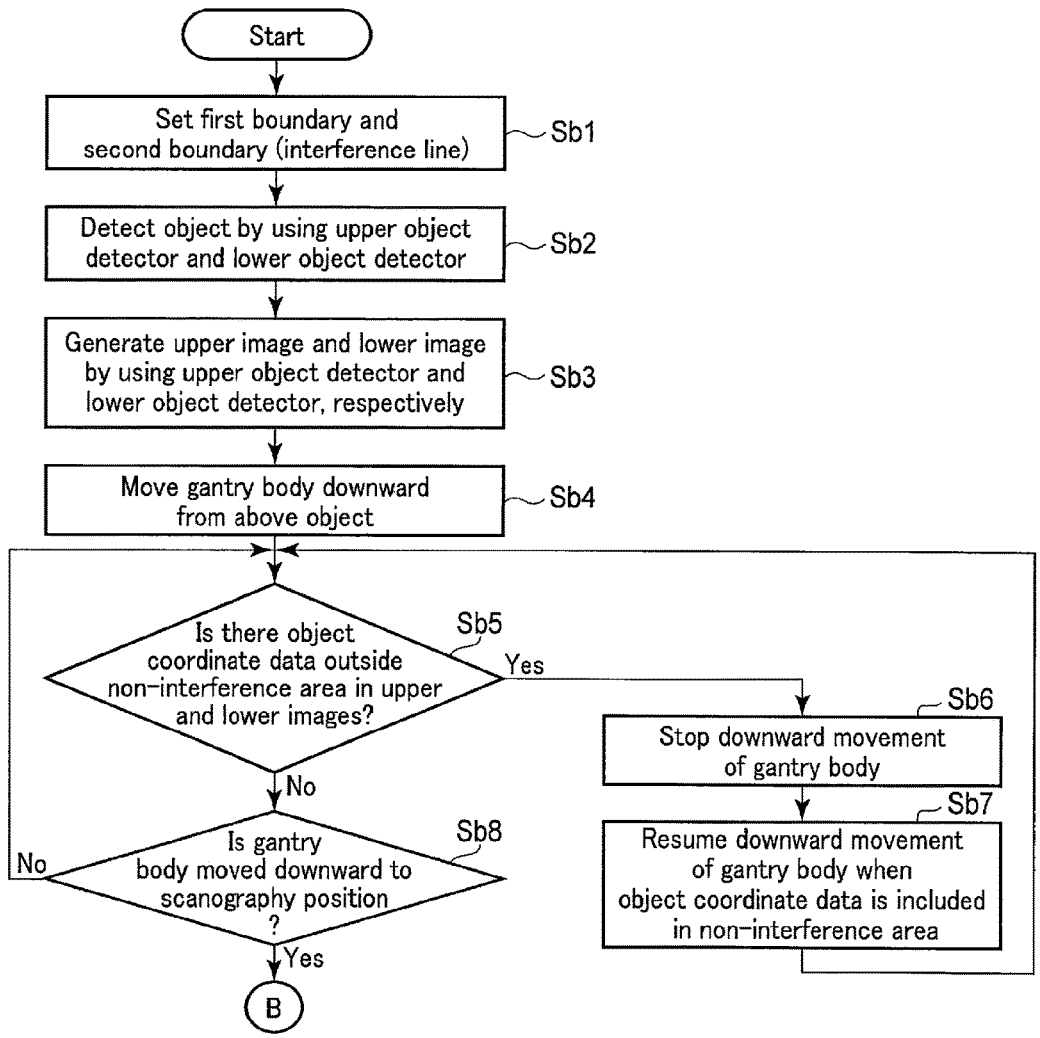
FIG. 9A is a flowchart showing a processing procedure for gantry control processing for scanogram acquisition according to the second embodiment.
Figure 9B:
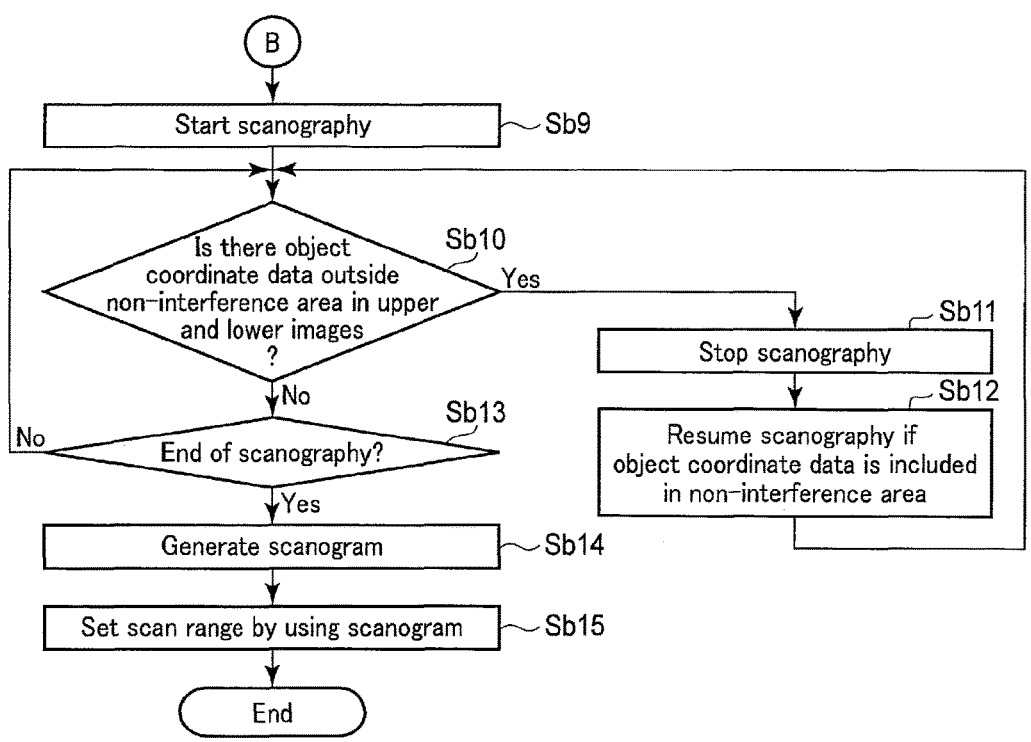
FIG. 9B is a flowchart showing a processing procedure for gantry control processing for scanogram acquisition according to the second embodiment.

FIGS. 9A and 9B are flowcharts showing an example of a processing procedure for gantry control processing concerning the acquisition of a scanogram.

A first boundary 151 and a second boundary 153 are set (step Sb1). A first upper object detector 161, a second upper object detector 163, the first lower object detector 451, and the second lower object detector 453 detect the object S (step Sb2). Note that if the object S is not detected by these object detectors, the subsequent processing is not executed.

After the processing in step Sb2, the first upper object detector 161 and the second upper object detector 163 respectively generate the first upper image and the second upper image. In addition, the first lower object detector 451 and the second lower object detector 453 respectively generate the first lower image and the second lower image (step Sb3). The first upper image, the second upper image, the first lower image, and the second lower image are generated and updated in real time, as needed.

At this time, object coordinate data are extracted from the upper and lower images. Object coordinate data concerning the first and second upper images (to be referred to as the upper image hereinafter) and the first and second lower images (to be referred to as the lower image hereinafter) are compared with the second boundary data. With this operation, if it is determined that the object coordinate data is included in the non-interference area, the gantry body 11 is moved downward to the scanography position in response to an instruction to move the gantry downward which is issued by the operator via the input device 59 (step Sb4).

If the object coordinate data is located outside the non-interference area in the upper and lower images (step Sb5), i.e., the object coordinate data is located outside a closed curve defined by the boundary data of the second boundary 153, the downward movement of the gantry body 11 is stopped (step Sb6). If the object coordinate data is included in the closed curve defined by the boundary data of the second boundary 153 and an instruction to resume the downward movement is input by the operator via the input device 59, the downward movement of the gantry body 11 is resumed (step Sb7).

If the object coordinate data is not located outside the non-interference area in the upper and lower images (step Sb5), the gantry body 11 is moved downward to the scanography position (step Sb8). In response to an instruction to resume the scanography issued by the operator via the input device 59, scanography is started (step Sb9).

If the object coordinate data is located outside the non-interference area (step Sb10), i.e., the object coordinate data is located outside a closed curve defined by the boundary data of the second boundary 153, scanography is stopped (step Sb11). If the object coordinate data is included in the non-interference area, i.e., the object coordinate data is included in the closed curve defined by the boundary data of the second boundary 153 and an instruction to resume the scanography is input by the operator via the input device 59, scanography is resumed (step Sb12).

If there is no object coordinate data outside the non-interference area (step Sb10), i.e., the object coordinate data is included in a closed curve defined by the boundary data of the second boundary 153, scanography is executed until the issuance of a scanography end instruction (step Sb13).

When the scanography is complete, a scanogram is generated (step Sb14). A scan range is set by using the scanogram in accordance with an instruction issued by the operator via the input device 59 (step Sb15). At this time, the position information of the gantry body 11 corresponding to the scan range is output to the system control circuitry 57. In addition, when the scan range is set, a non-scan target area (non-scan coordinate data) and a scan target area (scan target coordinate data) are set based on the upper and lower images concerning the scan range.

Figure 10:
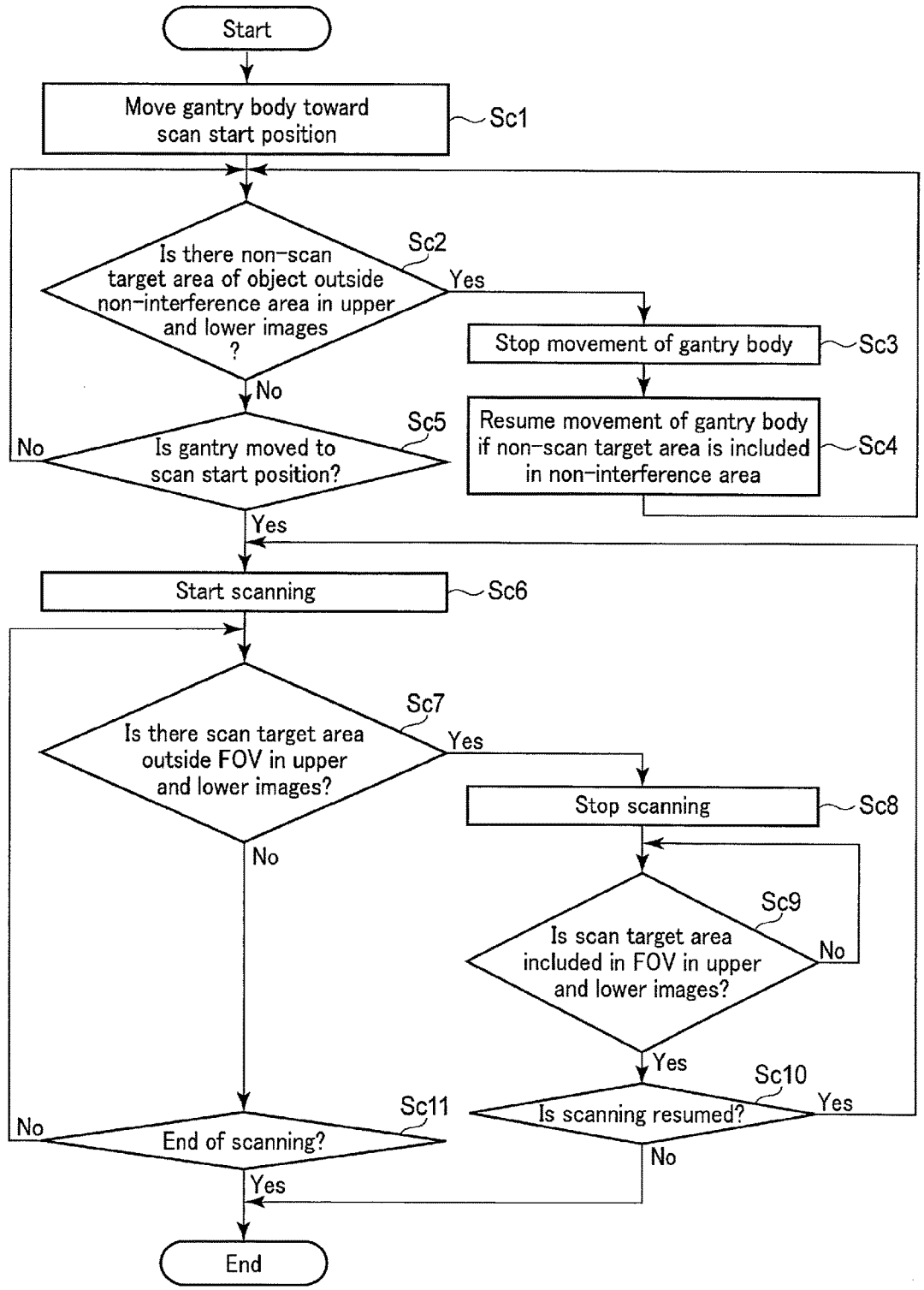
FIG. 10 is a flowchart showing gantry control processing in scanning executed after scanography according to the second embodiment.

FIG. 10 is a flowchart showing an example of gantry control processing in scanning executed after scanography.

If no object coordinate data is included outside the non-interference area, the gantry body 11 is moved toward the start position of the scan range (step Sc1). If the scan target area is located outside the non-interference area during the movement of the gantry body 11 (step Sc2), the movement of the gantry body 11 is stopped (step Sc3).

If the object coordinate data is included in the non-interference area, i.e., the object coordinate data is included in the inside of a closed curve defined by the boundary data of the second boundary 153 and an instruction to move the gantry body 11 is input by the operator via the input device 59, the movement of the gantry body 11 is resumed (step Sc4).

If the gantry body 11 has not moved to the scan start position, the processing in steps Sc2 to Sc4 is repeated (step Sc5). If the gantry body 11 has moved to the scan start position and the scan target area is included in the FOV, i.e., the scan target coordinate data is included in the inside (FOV) of a closed curve defined by the boundary data of the first boundary 151, scanning is started in accordance with a scan start instruction issued by the operator via the input device 59 (step Sc6).

If there is a scan target area outside the FOV (step Sc7), i.e., there is scan target coordinate data outside a closed curve defined by the boundary data of the first boundary 151, scanning is stopped (step Sc8). At this time, when scanning is helical scanning, the movement of the gantry body 11 is also stopped.

If the scan target area is included in the FOV (step Sc9), i.e., the scan target coordinate data is included in the inside (FOV) of a closed curve defined by the boundary data of the first boundary 151 and a scan resume instruction is input by the operator via the input device 59, the scanning is resumed (step Sc10). If the scanning is not resumed, the scanning is finished.

If there is no scan target area outside the FOV (step Sc7), i.e., the scan target coordinate data is included in the inside (FOV) of a closed curve defined by the boundary data of the first boundary 151, scanning is executed until the issuance of a scan end instruction (step Sc11).

According to the above arrangement, the following effects are obtained.

The X-ray computed tomography apparatus 2 according to this embodiment has a plurality of sensors (object detectors) installed in places excluding the gantry body 11, discriminates a scan target area and a non-scan target area by using scanograms generated by scanography, and determines, based on boundary position information and object position information associated with the gantry body 11, whether scan target coordinate data is included in the FOV. If the scan target area falls outside the FOV, the apparatus can stop scanning, and resume the scanning in accordance with an instruction issued by the operator when the scan target area returns into the FOV. That is, the X-ray computed tomography apparatus 2 according to the embodiment can decide the relative position relationship between the gantry body 11 and the object S based on scanograms and outputs from the object detectors.

In addition, the X-ray computed tomography apparatus 2 according to this embodiment can determine whether the non-scan target area falls outside the interference line to avoid interference with the gantry body 11, without mounting any object detector near the opening portion 15 of the gantry body 11, stop the downward movement of the gantry body 11 when the non-scan target area falls outside the interference line, and resume the downward movement of the gantry body 11 when the non-scan target area returns inside the interference line.

That is, the X-ray computed tomography apparatus 2 according to this embodiment can stop scanning and display a predetermined warning by deciding, based on scanograms and outputs from the object detectors, at which height the gantry body 11 is located relative to the object S, and determining whether an area outside the FOV is the scan target area. With this operation, the X-ray computed tomography apparatus 2 according to the embodiment can suppress the occurrence of unnecessary exposure of the object S and allows observation of a scan target area while securing safety for the object S without prolonging a scan time.

As described above, this embodiment can provide the X-ray computed tomography apparatus 1 which can reduce unnecessary exposure of the object S without interference between the object S and the gantry body 11.

(Third Embodiment)

Figure 13:
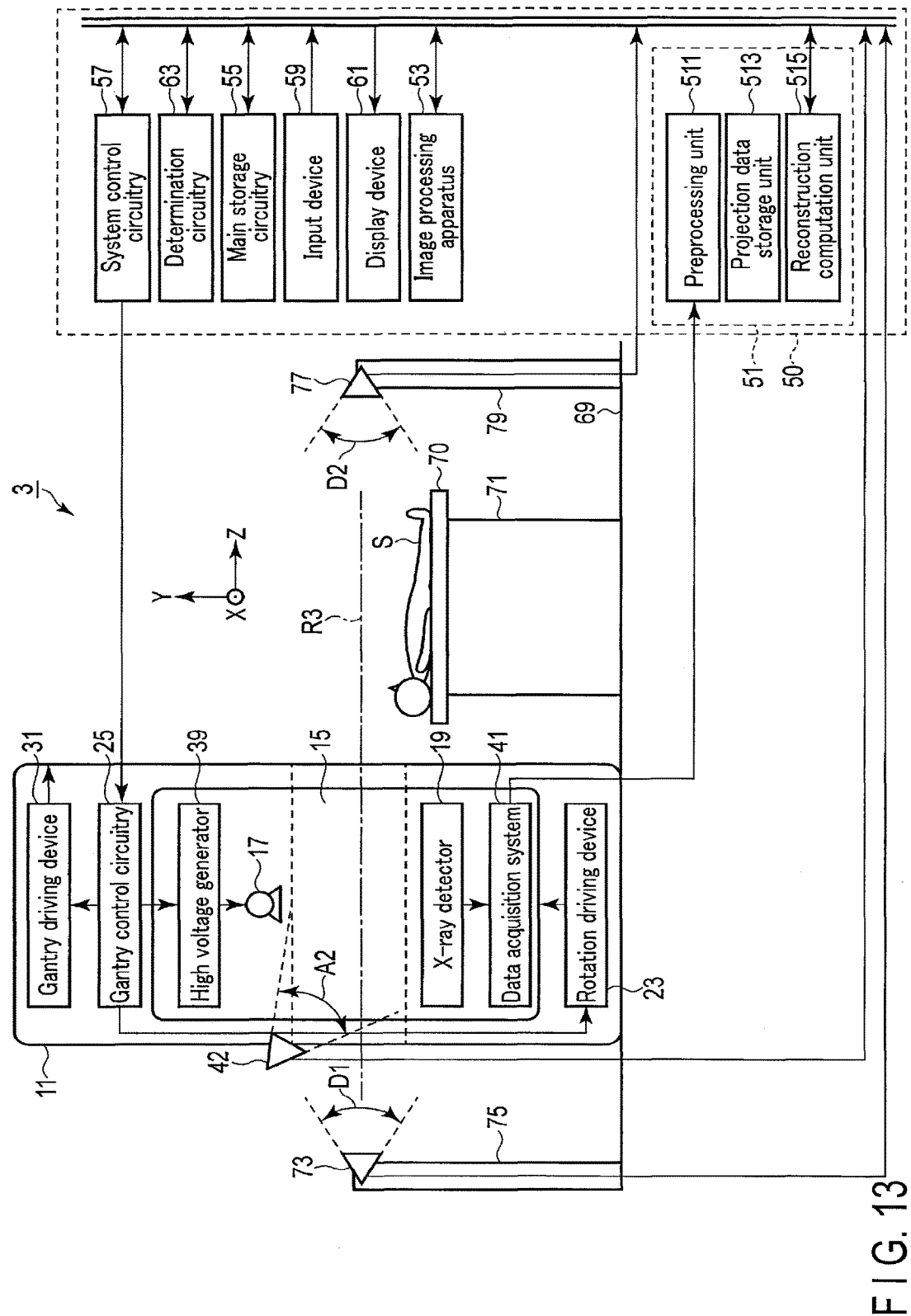
FIG. 13 is a block diagram showing the arrangement of an X-ray computed tomography apparatus according to the third embodiment.

A difference from the first and second embodiments is that an X-ray computed tomography apparatus capable of scanning an object in a prone position executes the above gantry control function. In the following description, the same reference numerals denote constituent elements having almost the same functions and arrangements, and a repetitive description will be made only when required. FIG. 13 is a block diagram showing an example of the arrangement of an X-ray computed tomography apparatus 3 according to this embodiment.

As shown in FIG. 13, a gantry body 11 of the X-ray computed tomography apparatus 3 is mounted on a floor surface 69 of an examination room. The X-ray computed tomography apparatus 3 includes a top 70 on which an object S is placed and a bed 71 which supports the top 70 so as to allow it be inserted into an opening portion 15. When performing scan imaging or scanography, the top 70 on which the object S is placed is inserted into the opening portion 15 under the control of a system control circuitry 57. The gantry body 11 may move along the Z direction so as to insert the top 70, on which the object S is placed, into the opening portion 15.

A posterior object detector 73 is provided at a position on an almost extended line of a rotation axis R3 without any tilt through a columnar support 75 at the back (rear surface) side of the gantry body 11 in place of the upper object detector 16. Note that the posterior object detector 73 may be provided at a position on an almost extended line of the rotation axis R3 without any tilt on the wall surface of the examination room. An anterior object detector 77 is provided at a position on an almost extended line of the rotation axis R3 without any tilt through a columnar support 79 on the front (front surface) side of the gantry body 11 in place of the lower object detector 45. Note that the anterior object detector 77 may be provided at a position on an almost extended line of the rotation axis R3 without any tilt on the wall surface of the examination room. In addition, the installation positions of the posterior object detector 73 and the anterior object detector 77 are not limited to positions on the extended line of the rotation axis R3 without any tilt.

The posterior object detector 73 and the anterior object detector 77 are devices which can detect the object S from the Z direction parallel to the rotation axis R3 without any tilt. The posterior object detector 73 and the anterior object detector 77 may detect end portions of the object S or a contour of the overall object S. The posterior object detector 73 and the anterior object detector 77 each are, for example, a camera (a movie camera or video camera). Note that the posterior object detector 73 and the anterior object detector 77 may have various types of distance sensors for deciding the distance between itself and the object S or various types of circuitry and an optical system which are associated with motion capturing (motion sensor) to detect the position of the object S.

The posterior object detector 73 and the anterior object detector 77 output information indicating whether the object S is detected, the relative positional relationship between the opening portion 15 and the object S, and the like to a console 50. The posterior object detector 73 and the anterior object detector 77 output a posterior image and an anterior image obtained by imaging the object S to the console 50. At this time, the relative positional relationship between the position of the object S and the gantry body 11 in the posterior image and the anterior image is specified.

As shown in FIG. 13, the posterior object detector 73 and the anterior object detector 77 respectively have a detection range D1 and a detection range D2 each capable of detecting the position of the object S. Note that the posterior object detector 73 and the anterior object detector 77 respectively may have the detection range D1 and the detection range D2 each capable of imaging a reference position or reference scale as a reference for the distance between itself and the object S. The reference position or reference scale is, for example, an object which is stationary at the time of the relative movement between the gantry body 11 and the top 70. The posterior object detector 73 and the anterior object detector 77 may measure the distance to the object S by detecting the reference scale.

(Gantry Control Function)

The gantry control function according this embodiment can be understood by replacing the upper object detector 16 with the posterior object detector 73, the lower object detector 45 with the anterior object detector 77, each upper image with a posterior image, and each lower image with an anterior image in the first embodiment and the modification. A description of this function will therefore be omitted. That is, the gantry control function according to the embodiment is the same as that of the X-ray computed tomography apparatuses 1 or 2 in FIGS. 1 and 7 as described when they are operated in a horizontal position.

Note that in this embodiment, the system control circuitry 57 and the like may control the movement of the top 70 instead of the gantry body 11. At this time, a control target is movement control of the top 70 instead of movement control of the gantry body 11 in the first embodiment and its modification. Note that a main storage circuitry 55 may store control modes in which the movement control of the gantry body 11 in the first and second modes is replaced with the movement control of the top 70. A description of the movement control of the top 70 corresponds to that when the movement control of the gantry body 11 is simply replaced with that of the top 70, and hence a description will be omitted.

The arrangement described above has the following effect in addition to the effect of other embodiments and modifications descried above.

According to the above arrangement, the X-ray computed tomography apparatus 3 according to this embodiment determines whether the non-scan target area falls outside the interference line to avoid interference with the gantry body 11. If the non-scan target area falls outside the interference line, the apparatus can stop moving the top 70. When the non-scan target area returns inside the interference line, the apparatus can resume the movement of the top 70. With the above operation, the embodiment can provide the X-ray computed tomography apparatus 3 which can reduce unnecessary exposure of the object S without any interference between the object S in a prone position and the gantry body 11.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray computed tomography apparatus, comprising:
    a gantry including an X-ray tube and an X-ray detector on both sides of an opening portion and configured to be relatively movable on a floor surface of an examination room to image an object with X-rays emitted from the X-ray tube;
    main storage circuitry configured to store information concerning a first boundary indicating an outer edge of a field of view inside the opening portion and information concerning a second boundary located between the first boundary and an inner surface of the opening portion to prevent interference between the object and the gantry;
    gantry control circuitry configured to control the X-ray tube so as to stop emitting X-rays based on a relative positional relationship between a scan target area of the object and the first boundary or to control the gantry so as to stop moving based on a relative positional relationship between a non-scan target area of the object and the second boundary;
    a plurality of object detectors configured to detect the object; and
    determination circuitry configured to determine, based on outputs from the plurality of object detectors, whether part of the scan target area is located outside a first area defined by the first boundary, and whether a part of the non-scan target area is located outside a second area defined by the second boundary, wherein the gantry control circuitry is further configured to control the gantry based on determination results obtained by the determination circuitry.

2. The apparatus according to claim 1, wherein the gantry control circuitry is further configured to control the X-ray tube so as to stop emitting X-rays when part of the scan target area exceeds the first boundary or control the gantry so as to stop moving when part of the non-scan target area exceeds the second boundary.

3. The apparatus according to claim 1, wherein when it is determined, in scanning the object, that part of the scan target area is located outside the first area or part of the non-scan target area is located outside the second area, the gantry control circuitry is further configured to control the gantry to stop the scanning and the movement of the gantry.

4. The apparatus according to claim 3, wherein the gantry control circuitry is further configured to control the gantry to resume the scanning in response to an input of an instruction to resume the scanning and a timing at which the scan target area is included in an area defined by the first boundary after stoppage of the scanning.

5. The apparatus according to claim 1, wherein the gantry is further configured to scan the object in a standing position or a sitting position,
  the plurality of object detectors are provided on at least one of an upper side and a lower side of the opening portion and the outer edge on an exterior of the gantry, and
  the non-scan target area is an area in which an object detector, of the plurality of object detectors, provided on the outer edge is unable to detect the object.

6. The apparatus according to claim 1, wherein the gantry is further configured to scan the object in a standing position or a sitting position and perform scanography on the object,
  the plurality of object detectors are provided on an upper side and a lower side of the opening portion,
  the field of view is set by using a scanogram obtained by the scanography, and
  the non-scan target area is an area in which the scanogram is inconsistent with the object detected by the plurality of object detectors.

7. The apparatus according to claim 1, wherein each object detector is at least one of a camera, a detector using an acoustic wave, a detector using infrared light, and a detector using a magnetic field.

8. The apparatus according to claim 1, wherein each object detector is configured to detect an end portion of the object or a contour of the object.

9. An X-ray computed tomography apparatus, comprising:
  a gantry including an X-ray tube and an X-ray detector on both sides of an opening portion and configured to be relatively movable on a floor surface of an examination room to image an object with X-rays emitted from the X-ray tube;
  main storage circuitry to store information concerning a first boundary indicating an outer edge of a field of view inside the opening portion and information concerning a second boundary located between the first boundary and an inner surface of the opening portion to prevent interference between the object and the gantry; and
  gantry control circuitry configured to control the X-ray tube so as to stop emitting X-rays based on a relative positional relationship between a scan target area of the object and the first boundary or to control the gantry so as to stop moving based on a relative positional relationship between a non-scan target area of the object and the second boundary,
  wherein the main storage circuitry is further configured to store a first control mode of controlling the X-ray tube so as to stop emitting X-rays when part of the scan target area exceeds the first boundary or controlling the gantry so as to stop moving when part of the non-scan target area exceeds the second boundary, and store a second control mode of controlling the gantry so as to stop moving when a contour of the object exceeds the second boundary, and
  the gantry control circuitry is further configured to control the gantry in the second control mode when the field of view changed by a setting made by an operator or tilting of the gantry relative to the floor surface is narrower than the contour, and control the gantry in the first control mode when the field of view changed by the setting or the tilting is wider than the contour.

* * * * *